| (12) | United States Patent<br>Connor | (10) Patent No.: US 11,357,511 B2<br>(45) Date of Patent: \*Jun. 14, 2022 |
|---|---|---|

(54) INTRASACULAR ANEURYSM OCCLUSION DEVICE WITH GLOBULAR FIRST CONFIGURATION AND BOWL-SHAPED SECOND CONFIGURATION

(71) Applicant: Robert A. Connor, St. Paul, MN (US)

(72) Inventor: Robert A. Connor, St. Paul, MN (US)

(73) Assignee: Aneuclose LLC, St. Paul, MN (US)

( \* ) Notice: Subject to any disclaimer, the term of this patent is extended or adjusted under 35 U.S.C. 154(b) by 0 days.

This patent is subject to a terminal disclaimer.

(21) Appl. No.: 17/466,497

(22) Filed: Sep. 3, 2021

(65) Prior Publication Data

US 2021/0393270 A1    Dec. 23, 2021

Related U.S. Application Data

(63) Continuation-in-part of application No. 17/220,002, filed on Apr. 1, 2021, and a continuation-in-part of application No. 17/214,827, filed on Mar. 27, 2021, and a continuation-in-part of application No. 17/211,446, filed on Mar. 24, 2021, and a continuation-in-part of application No. 16/693,267, filed on Nov. 23, 2019, and a continuation-in-part of application No. 16/660,929, filed on Oct. 23, 2019, said application No. 16/693,267 is a continuation-in-part of application No. 16/660,929, filed on Oct. 23, 2019, and a continuation-in-part of (Continued)

(51) Int. Cl.
*A61B 17/12* (2006.01)

(52) U.S. Cl.
CPC .. *A61B 17/12118* (2013.01); *A61B 17/12168* (2013.01); *A61B 2017/1205* (2013.01)

(58) Field of Classification Search
CPC ........ A61B 17/12118; A61B 17/12113; A61B 17/12177; A61B 17/12168; A61B 2017/1205; A61B 17/12099
See application file for complete search history.

(56) References Cited

U.S. PATENT DOCUMENTS 6,454,780 B1 \* 9/2002 Wallace ........... A61B 17/12022
606/151
7,695,488 B2 \* 4/2010 Berenstein ....... A61B 17/12177
606/191

(Continued)

OTHER PUBLICATIONS

U.S. Appl. No. 61/483,032, filed May 5, 2011, Kent et al.

(Continued)

*Primary Examiner* — Diane D Yabut
*Assistant Examiner* — Christina C Lauer

(57) ABSTRACT

This invention is an intrasacular aneurysm occlusion device with a proximal stent which is expanded to a globular shape within an aneurysm sac and then compressed into a bowl shape which covers the aneurysm neck. The device further comprises embolic members and/or embolic material which is inserted into a distal portion of the aneurysm sac. The proximal stent component covers the aneurysm neck so as to reduce blood flow into the aneurysm sac and the accumulated embolic members and/or embolic material in the distal portion of the aneurysm sac keeps the proximal stent in place.

3 Claims, 4 Drawing Sheets

Related U.S. Application Data application No. 16/541,241, filed on Aug. 15, 2019, now abandoned, and a continuation-in-part of application No. 15/865,822, filed on Jan. 9, 2018, now Pat. No. 10,716,573, and a continuation-in-part of application No. 15/861,482, filed on Jan. 3, 2018, now abandoned, said application No. 16/660,929 is a continuation-in-part of application No. 16/541,241, filed on Aug. 15, 2019, now abandoned, and a continuation-in-part of application No. 15/865,822, filed on Jan. 9, 2018, now Pat. No. 10,716,573, and a continuation-in-part of application No. 15/861,482, filed on Jan. 3, 2018, now abandoned, said application No. 16/541,241 is a continuation-in-part of application No. 15/865,822, filed on Jan. 9, 2018, now Pat. No. 10,716,573, which is a continuation-in-part of application No. 15/081,909, filed on Mar. 27, 2016, now abandoned, and a continuation-in-part of application No. 14/526,600, filed on Oct. 29, 2014, now abandoned, said application No. 15/861,482 is a continuation-in-part of application No. 15/080,915, filed on Mar. 25, 2016, now Pat. No. 10,028,747, and a continuation-in-part of application No. 14/526,600, filed on Oct. 29, 2014, now abandoned, said application No. 15/081,909 is a continuation-in-part of application No. 14/526,600, filed on Oct. 29, 2014, now abandoned, said application No. 15/080,915 is a continuation-in-part of application No. 14/526,600, filed on Oct. 29, 2014, now abandoned, which is a continuation-in-part of application No. 12/989,048, filed on Oct. 21, 2010, now Pat. No. 8,974,487.

(60) Provisional application No. 63/119,774, filed on Dec. 1, 2020, provisional application No. 62/794,609, filed on Jan. 19, 2019, provisional application No. 62/794,607, filed on Jan. 19, 2019, provisional application No. 62/720,173, filed on Aug. 21, 2018, provisional application No. 62/589,754, filed on Nov. 22, 2017, provisional application No. 62/472,519, filed on Mar. 16, 2017, provisional application No. 62/444,860, filed on Jan. 11, 2017, provisional application No. 61/897,245, filed on Oct. 30, 2013, provisional application No. 61/126,047, filed on May 1, 2008, provisional application No. 61/126,027, filed on May 1, 2008.

(56) References Cited

U.S. PATENT DOCUMENTS

| | | | |
|---|---|---|---|
| 8,142,456 B2 * | 3/2012 | Rosqueta | A61B 17/12118 606/157 |
| 8,597,320 B2 | 12/2013 | Sepetka et al. | |
| 8,974,512 B2 | 3/2015 | Aboytes et al. | |
| 8,998,947 B2 | 4/2015 | Aboytes et al. | |
| 9,039,726 B2 | 5/2015 | Becking | |
| 9,078,658 B2 | 7/2015 | Hewitt et al. | |
| 9,492,174 B2 | 11/2016 | Hewitt et al. | |
| 9,585,669 B2 | 3/2017 | Becking et al. | |
| 9,629,635 B2 | 4/2017 | Hewitt et al. | |
| 9,955,976 B2 | 5/2018 | Hewitt et al. | |
| 9,980,733 B2 | 5/2018 | Badruddin et al. | |
| 10,130,372 B2 | 11/2018 | Griffin | |
| 10,265,075 B2 | 4/2019 | Porter et al. | |
| 10,285,711 B2 | 5/2019 | Griffin | |
| 10,314,593 B2 | 6/2019 | Bardsley et al. | |
| 10,327,781 B2 | 6/2019 | Divino et al. | |
| 10,383,635 B2 | 8/2019 | Wallace et al. | |
| 10,398,441 B2 | 9/2019 | Warner et al. | |
| 10,426,486 B2 | 10/2019 | Guo et al. | |
| 10,433,853 B2 | 10/2019 | Divino et al. | |
| 10,595,875 B2 | 3/2020 | Mayer et al. | |
| 10,610,231 B2 | 4/2020 | Marchand et al. | |
| 10,617,426 B2 | 4/2020 | Aboytes et al. | |
| 10,617,427 B2 | 4/2020 | Aboytes et al. | |
| 10,653,425 B1 | 5/2020 | Gorochow et al. | |
| 10,675,036 B2 | 6/2020 | Rosqueta et al. | |
| 10,675,037 B2 | 6/2020 | Aboytes et al. | |
| 10,716,573 B2 * | 7/2020 | Connor | A61B 17/12163 |
| 10,716,574 B2 | 7/2020 | Lorenzo et al. | |
| 10,729,447 B2 | 8/2020 | Shimizu et al. | |
| 10,736,758 B2 | 8/2020 | Ruvalcaba et al. | |
| 10,751,066 B2 | 8/2020 | Lorenzo | |
| 10,813,645 B2 | 10/2020 | Hewitt et al. | |
| 10,856,880 B1 | 12/2020 | Badruddin et al. | |
| 10,869,672 B2 | 12/2020 | Griffin | |
| 10,881,413 B2 | 1/2021 | Merritt et al. | |
| 10,898,200 B2 | 1/2021 | Aboytes et al. | |
| 10,905,430 B2 | 2/2021 | Lorenzo et al. | |
| 10,905,431 B2 | 2/2021 | Gorochow | |
| 10,925,612 B2 | 2/2021 | Wallace et al. | |
| 10,939,914 B2 | 3/2021 | Hewitt et al. | |
| 10,939,915 B2 | 3/2021 | Gorochow et al. | |
| 10,939,916 B2 | 3/2021 | Aboytes et al. | |
| 10,952,739 B2 | 3/2021 | Plaza et al. | |
| 10,952,878 B2 | 3/2021 | Kusleika | |
| 10,980,545 B2 | 4/2021 | Bowman et al. | |
| 11,013,516 B2 | 5/2021 | Franano et al. | |
| 11,033,275 B2 | 6/2021 | Franano et al. | |
| 11,033,277 B2 | 6/2021 | Wolfe et al. | |
| 11,045,203 B2 | 6/2021 | Sepetka et al. | |
| 11,051,825 B2 | 7/2021 | Gorochow | |
| 11,058,430 B2 | 7/2021 | Gorochow et al. | |
| 11,058,431 B2 | 7/2021 | Pereira et al. | |
| 11,071,551 B2 | 7/2021 | Garza et al. | |
| 11,076,860 B2 | 8/2021 | Lorenzo | |
| 11,076,861 B2 | 8/2021 | Gorochow et al. | |
| 2002/0169473 A1 | 11/2002 | Sepetka et al. | |
| 2006/0155323 A1 | 7/2006 | Porter et al. | |
| 2008/0281350 A1 | 11/2008 | Sepetka et al. | |
| 2009/0287294 A1 | 11/2009 | Rosqueta et al. | |
| 2011/0022149 A1 | 1/2011 | Cox et al. | |
| 2011/0208227 A1 | 8/2011 | Becking | |
| 2012/0165919 A1 | 6/2012 | Cox et al. | |
| 2012/0239074 A1 | 9/2012 | Aboytes et al. | |
| 2012/0283768 A1 | 11/2012 | Cox et al. | |
| 2013/0245667 A1 | 9/2013 | Marchand et al. | |
| 2014/0052233 A1 | 2/2014 | Cox et al. | |
| 2014/0135812 A1 | 5/2014 | Divino et al. | |
| 2014/0358178 A1 | 12/2014 | Hewitt et al. | |
| 2015/0209050 A1 | 7/2015 | Aboytes et al. | |
| 2015/0216684 A1 | 8/2015 | Enzmann et al. | |
| 2015/0272589 A1 | 10/2015 | Lorenzo | |
| 2015/0272590 A1 | 10/2015 | Aboytes et al. | |
| 2015/0297240 A1 | 10/2015 | Divino et al. | |
| 2015/0313605 A1 | 11/2015 | Griffin | |
| 2016/0022275 A1 | 1/2016 | Garza | |
| 2016/0022445 A1 | 1/2016 | Ruvalcaba et al. | |
| 2016/0213380 A1 | 7/2016 | O'Brien et al. | |
| 2016/0249934 A1 | 9/2016 | Hewitt et al. | |
| 2016/0249935 A1 | 9/2016 | Hewitt et al. | |
| 2016/0249937 A1 | 9/2016 | Marchand et al. | |
| 2016/0262766 A1 | 9/2016 | Aboytes et al. | |
| 2016/0367260 A9 | 12/2016 | Hewitt et al. | |
| 2017/0079661 A1 | 3/2017 | Bardsley et al. | |
| 2017/0079662 A1 | 3/2017 | Rhee et al. | |
| 2017/0086851 A1 | 3/2017 | Wallace et al. | |
| 2017/0095254 A1 | 5/2017 | Hewitt et al. | |
| 2017/0128077 A1 | 5/2017 | Hewitt et al. | |
| 2017/0156733 A1 | 6/2017 | Becking et al. | |
| 2017/0156734 A1 | 6/2017 | Griffin | |
| 2017/0189035 A1 | 7/2017 | Porter | |
| 2017/0258473 A1 | 9/2017 | Plaza et al. | |
| 2017/0281194 A1 | 10/2017 | Divino et al. | |
| 2017/0354418 A1 | 12/2017 | Teoh et al. | |
| 2018/0000489 A1 | 1/2018 | Marchand et al. | |
| 2018/0036012 A1 | 2/2018 | Aboytes et al. | |
| 2018/0070955 A1 | 3/2018 | Greene et al. | |

(56) References Cited

U.S. PATENT DOCUMENTS

| | | |
|---|---|---|
| 2018/0092690 A1 | 4/2018 | Priya et al. |
| 2018/0132859 A1 | 5/2018 | Aboytes et al. |
| 2018/0132862 A1 | 5/2018 | Aboytes et al. |
| 2018/0206849 A1 | 7/2018 | Hewitt et al. |
| 2018/0242979 A1 | 8/2018 | Lorenzo |
| 2018/0250013 A1 | 9/2018 | Wallace et al. |
| 2018/0271540 A1 | 9/2018 | Merritt et al. |
| 2018/0303486 A1 | 10/2018 | Rosenbluth et al. |
| 2019/0008522 A1 | 1/2019 | Lorenzo |
| 2019/0053810 A1 | 2/2019 | Griffin |
| 2019/0053811 A1 | 2/2019 | Garza et al. |
| 2019/0059909 A1 | 2/2019 | Griffin |
| 2019/0105054 A1 | 4/2019 | Aboytes et al. |
| 2019/0105056 A1 | 4/2019 | Aboytes et al. |
| 2019/0133794 A1 | 5/2019 | Kusleika |
| 2019/0192166 A1 | 6/2019 | Hewitt et al. |
| 2019/0192168 A1 | 6/2019 | Lorenzo et al. |
| 2019/0201000 A1 | 7/2019 | Wallace et al. |
| 2019/0209178 A1 | 7/2019 | Richter et al. |
| 2019/0209181 A1 | 7/2019 | Mayer et al. |
| 2019/0216467 A1 | 7/2019 | Goyal |
| 2019/0223878 A1 | 7/2019 | Lorenzo et al. |
| 2019/0223881 A1 | 7/2019 | Hewitt et al. |
| 2019/0254676 A1 | 8/2019 | Murphy et al. |
| 2019/0262002 A1 | 8/2019 | Benjamin |
| 2019/0269411 A1 | 9/2019 | Bardsley et al. |
| 2019/0269414 A1 | 9/2019 | Griffin |
| 2019/0274691 A1 | 9/2019 | Sepetka et al. |
| 2019/0282242 A1 | 9/2019 | Divino et al. |
| 2019/0290286 A1 | 9/2019 | Divino et al. |
| 2019/0298379 A1 | 10/2019 | Porter et al. |
| 2019/0307460 A1 | 10/2019 | Ferrera et al. |
| 2019/0307546 A1 | 10/2019 | Aguilar et al. |
| 2019/0343532 A1 | 11/2019 | Divino et al. |
| 2019/0343664 A1 | 11/2019 | Ruvalcaba et al. |
| 2019/0350590 A1 | 11/2019 | Aboytes et al. |
| 2019/0362496 A1 | 11/2019 | Dutta et al. |
| 2019/0365385 A1 | 12/2019 | Gorochow et al. |
| 2019/0365472 A1 | 12/2019 | Connor |
| 2019/0374228 A1 | 12/2019 | Wallace et al. |
| 2020/0038032 A1 | 2/2020 | Rhee et al. |
| 2020/0038035 A1 | 2/2020 | Griffin |
| 2020/0113576 A1 | 4/2020 | Gorochow et al. |
| 2020/0138447 A1 | 5/2020 | Rosqueta et al. |
| 2020/0155333 A1 | 5/2020 | Franano et al. |
| 2020/0163677 A1 | 5/2020 | Mayer et al. |
| 2020/0163784 A1 | 5/2020 | Franano et al. |
| 2020/0187952 A1 | 6/2020 | Walsh et al. |
| 2020/0187953 A1 | 6/2020 | Hamel et al. |
| 2020/0187954 A1 | 6/2020 | Hamel et al. |
| 2020/0197017 A1 | 6/2020 | Hamel et al. |
| 2020/0197018 A1 | 6/2020 | Hamel et al. |
| 2020/0197020 A1 | 6/2020 | Hamel et al. |
| 2020/0205841 A1 | 7/2020 | Aboytes et al. |
| 2020/0281603 A1 | 9/2020 | Marchand et al. |
| 2020/0289124 A1 | 9/2020 | Rangwala et al. |
| 2020/0289125 A1 | 9/2020 | Dholakia et al. |
| 2020/0289126 A1 | 9/2020 | Hewitt et al. |
| 2020/0360025 A1 | 11/2020 | Wallace et al. |
| 2020/0367893 A1 | 11/2020 | Xu et al. |
| 2020/0367898 A1 | 11/2020 | Gorochow et al. |
| 2020/0367900 A1 | 11/2020 | Pedroso et al. |
| 2020/0367901 A1 | 11/2020 | Porter et al. |
| 2020/0367906 A1 | 11/2020 | Xu et al. |
| 2020/0375606 A1 | 12/2020 | Lorenzo |
| 2020/0375607 A1 | 12/2020 | Soto Del Valle et al. |
| 2020/0397447 A1 | 12/2020 | Lorenzo et al. |
| 2020/0405347 A1 | 12/2020 | Walzman |
| 2021/0007754 A1 | 1/2021 | Milhous et al. |
| 2021/0007755 A1 | 1/2021 | Lorenzo et al. |
| 2021/0022765 A1 | 1/2021 | Walzman |
| 2021/0045750 A1 | 2/2021 | Wolf et al. |
| 2021/0052278 A1 | 2/2021 | Mauger |
| 2021/0052279 A1 | 2/2021 | Porter et al. |
| 2021/0068842 A1 | 3/2021 | Griffin |
| 2021/0069387 A1 | 3/2021 | Chen et al. |
| 2021/0085333 A1 | 3/2021 | Gorochow et al. |
| 2021/0106337 A1 | 4/2021 | Hewitt et al. |
| 2021/0106338 A1 | 4/2021 | Gorochow |
| 2021/0128160 A1 | 5/2021 | Li et al. |
| 2021/0128162 A1 | 5/2021 | Rhee et al. |
| 2021/0128165 A1 | 5/2021 | Pulugurtha et al. |
| 2021/0128167 A1 | 5/2021 | Patel et al. |
| 2021/0128168 A1 | 5/2021 | Nguyen et al. |
| 2021/0128169 A1 | 5/2021 | Li et al. |
| 2021/0129275 A1 | 5/2021 | Nguyen et al. |
| 2021/0137526 A1 | 5/2021 | Lee et al. |
| 2021/0137529 A1 | 5/2021 | Chen |
| 2021/0137715 A1 | 5/2021 | Ringwala et al. |
| 2021/0145449 A1 | 5/2021 | Gorochow |
| 2021/0153871 A1 | 5/2021 | Griffin |
| 2021/0153872 A1 | 5/2021 | Nguyen et al. |
| 2021/0169495 A1 | 6/2021 | Gorochow et al. |
| 2021/0169496 A1 | 6/2021 | Badruddin et al. |
| 2021/0169498 A1 | 6/2021 | Gorochow |
| 2021/0169499 A1 | 6/2021 | Merritt et al. |
| 2021/0177429 A1 | 6/2021 | Lorenzo |
| 2021/0186518 A1 | 6/2021 | Gorochow et al. |
| 2021/0196284 A1 | 7/2021 | Gorochow et al. |
| 2021/0204955 A1 | 7/2021 | Wallace et al. |
| 2021/0219982 A1 | 7/2021 | Badruddin et al. |
| 2021/0228214 A1 | 7/2021 | Bowman et al. |
| 2021/0244420 A1 | 8/2021 | Aboytes et al. |
| 2021/0251635 A1 | 8/2021 | Soto Del Valle et al. |
| 2021/0259699 A1 | 8/2021 | Rosenbluth et al. |
| 2021/0275184 A1 | 9/2021 | Hewitt et al. |
| 2021/0275187 A1 | 9/2021 | Franano et al. |
| 2021/0275188 A1 | 9/2021 | Plaza et al. |
| 2021/0275779 A1 | 9/2021 | Northrop |
| 2021/0282784 A1 | 9/2021 | Sepetka et al. |
| 2021/0282785 A1 | 9/2021 | Dholakia et al. |
| 2021/0282786 A1 | 9/2021 | Zaidat et al. |
| 2021/0282789 A1 | 9/2021 | Vu et al. |
| 2021/0282944 A1 | 9/2021 | Chen et al. |

OTHER PUBLICATIONS

U.S. Appl. No. 61/866,993, filed Aug. 16, 2013, Hewitt et al.
U.S. Appl. No. 61/979,416, filed Apr. 14, 2014, Hewitt et al.
U.S. Appl. No. 62/093,313, filed Dec. 17, 2014, Hewitt et al.
U.S. Appl. No. 62/307,123, filed Mar. 11, 2016, Plaza et al.
U.S. Appl. No. 62/819,296, filed Mar. 15, 2019, Rangwala et al.
U.S. Appl. No. 62/819,317, filed Mar. 15, 2019, Dholakia et al.
U.S. Appl. No. 62/873,256, filed Jul. 12, 2019, Milhous et al.

* cited by examiner

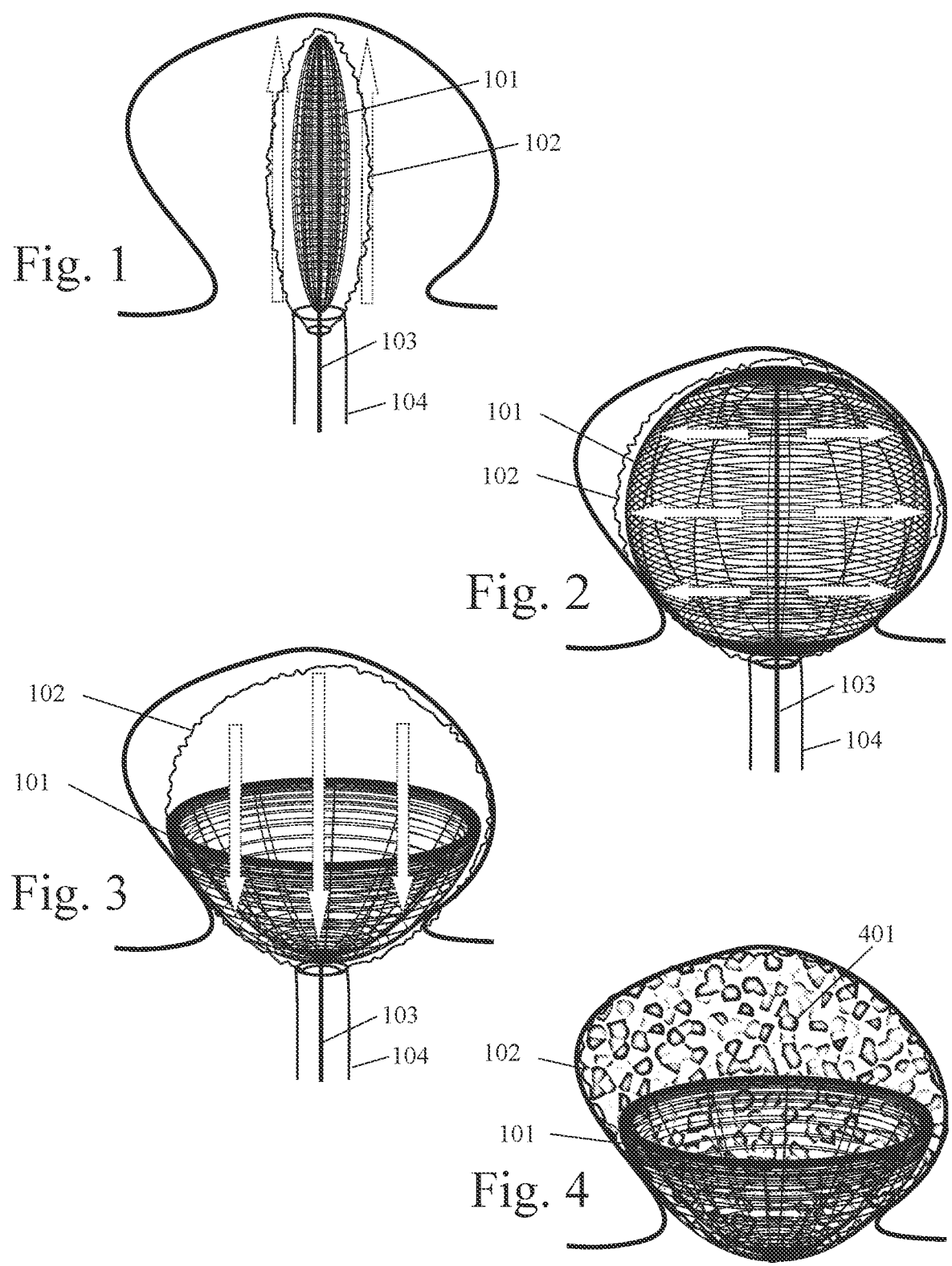

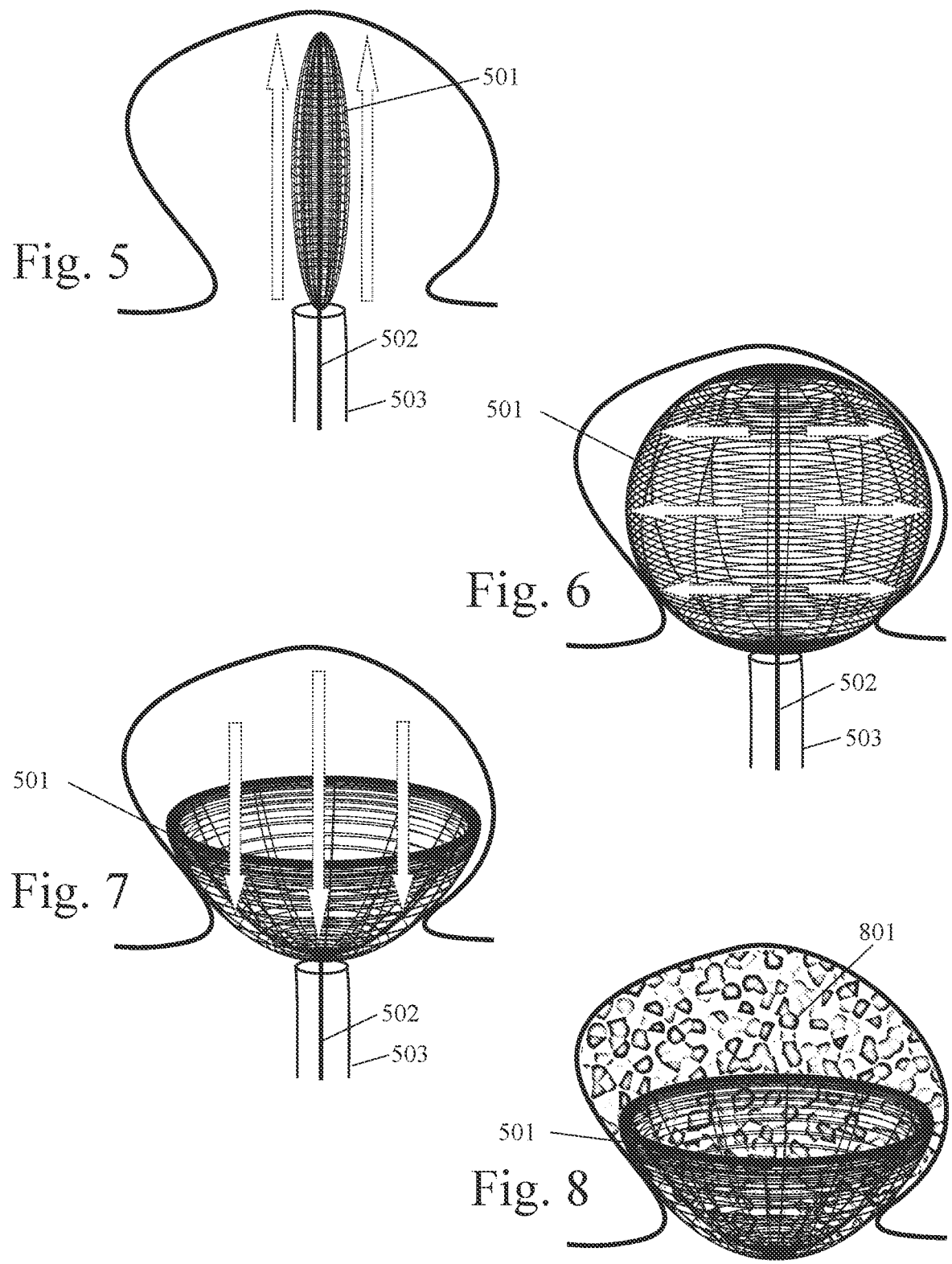

INTRASACULAR ANEURYSM OCCLUSION DEVICE WITH GLOBULAR FIRST CONFIGURATION AND BOWL-SHAPED SECOND CONFIGURATION

CROSS-REFERENCE TO RELATED APPLICATIONS

This present application is a continuation-in-part of patent application Ser. No. 17/220,002 filed on 2021 Apr. 1. This present application is also a continuation-in-part of patent application Ser. No. 17/214,827 filed on 2021 Mar. 27. This present application is also a continuation-in-part of patent application Ser. No. 17/211,446 filed on 2021 Mar. 24. This present application claims the priority benefit of provisional patent application 63/119,774 filed on 2020 Dec. 1. This present application is also a continuation-in-part of patent application Ser. No. 16/693,267 filed on 2019 Nov. 23. This present application is also a continuation-in-part of patent application Ser. No. 16/660,929 filed on 2019 Oct. 23.

Application Ser. No. 16/693,267 is a continuation-in-part of patent application Ser. No. 16/660,929 filed on 2019 Oct. 23. application Ser. No. 16/693,267 claimed the priority benefit of provisional patent application 62/794,609 filed on 2019 Jan. 19. application Ser. No. 16/693,267 claimed the priority benefit of provisional patent application 62/794,607 filed on 2019 Jan. 19. application Ser. No. 16/693,267 was a continuation-in-part of patent application Ser. No. 16/541,241 filed on 2019 Aug. 15. application Ser. No. 16/693,267 was a continuation-in-part of patent application Ser. No. 15/865,822 filed on 2018 Jan. 9 and issued as U.S. Pat. No. 10,716,573 on 2020 Jul. 21. application Ser. No. 16/693,267 was a continuation-in-part of patent application Ser. No. 15/861,482 filed on 2018 Jan. 3.

Application Ser. No. 16/660,929 claimed the priority benefit of provisional patent application 62/794,609 filed on 2019 Jan. 19. application Ser. No. 16/660,929 claimed the priority benefit of provisional patent application 62/794,607 filed on 2019 Jan. 19. application Ser. No. 16/660,929 was a continuation-in-part of patent application Ser. No. 16/541,241 filed on 2019 Aug. 15. application Ser. No. 16/660,929 was a continuation-in-part of patent application Ser. No. 15/865,822 filed on 2018 Jan. 9 and issued as U.S. Pat. No. 10,716,573 on 2020 Jul. 21. application Ser. No. 16/660,929 was a continuation-in-part of patent application Ser. No. 15/861,482 filed on 2018 Jan. 3.

Application Ser. No. 16/541,241 claimed the priority benefit of provisional patent application 62/794,609 filed on 2019 Jan. 19. application Ser. No. 16/541,241 claimed the priority benefit of provisional patent application 62/794,607 filed on 2019 Jan. 19. application Ser. No. 16/541,241 claimed the priority benefit of provisional patent application 62/720,173 filed on 2018 Aug. 21. application Ser. No. 16/541,241 was a continuation-in-part of patent application Ser. No. 15/865,822 filed on 2018 Jan. 9 and issued as U.S. Pat. No. 10,716,573 on 2020 Jul. 21.

Application Ser. No. 15/865,822 claimed the priority benefit of provisional patent application 62/589,754 filed on 2017 Nov. 22. application Ser. No. 15/865,822 claimed the priority benefit of provisional patent application 62/472,519 filed on 2017 Mar. 16. application Ser. No. 15/865,822 was a continuation-in-part of patent application Ser. No. 15/081,909 filed on 2016 Mar. 27. application Ser. No. 15/865,822 was a continuation-in-part of patent application Ser. No. 14/526,600 filed on 2014 Oct. 29.

Application Ser. No. 15/861,482 claimed the priority benefit of provisional patent application 62/589,754 filed on 2017 Nov. 22. application Ser. No. 15/861,482 claimed the priority benefit of provisional patent application 62/472,519 filed on 2017 Mar. 16. application Ser. No. 15/861,482 claimed the priority benefit of provisional patent application 62/444,860 filed on 2017 Jan. 11. application Ser. No. 15/861,482 was a continuation-in-part of patent application Ser. No. 15/080,915 filed on 2016 Mar. 25 and issued as U.S. Pat. No. 10,028,747 on 2018 Jul. 24. application Ser. No. 15/861,482 was a continuation-in-part of patent application Ser. No. 14/526,600 filed on 2014 Oct. 29.

Application Ser. No. 15/081,909 was a continuation-in-part of patent application Ser. No. 14/526,600 filed on 2014 Oct. 29. application Ser. No. 15/080,915 was a continuation-in-part of patent application Ser. No. 14/526,600 filed on 2014 Oct. 29. application Ser. No. 14/526,600 claimed the priority benefit of provisional patent application 61/897,245 filed on 2013 Oct. 30. application Ser. No. 14/526,600 was a continuation-in-part of patent application Ser. No. 12/989,048 filed on 2010 Oct. 21 and issued as U.S. Pat. No. 8,974,487 on 2015 Mar. 10. application Ser. No. 12/989,048 claimed the priority benefit of provisional patent application 61/126,047 filed on 2008 May 1. application Ser. No. 12/989,048 claimed the priority benefit of provisional patent application 61/126,027 filed on 2008 May 1.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices for occluding cerebral aneurysms.

INTRODUCTION

An aneurysm is an abnormal bulging of a blood vessel wall. The vessel from which the aneurysm protrudes is the parent vessel. Saccular aneurysms look like a sac protruding out from the parent vessel. Saccular aneurysms have a neck and can be prone to rupture. Fusiform aneurysms are a form of aneurysm in which a blood vessel is expanded circumferentially in all directions. Fusiform aneurysms generally do not have a neck and are less prone to rupturing than saccular aneurysms. As an aneurysm grows larger, its walls generally become thinner and weaker. This decrease in wall integrity, particularly for saccular aneurysms, increases the risk of the aneurysm rupturing and hemorrhaging blood into the surrounding tissue, with serious and potentially fatal health outcomes.

Cerebral aneurysms, also called brain aneurysms or intracranial aneurysms, are aneurysms that occur in the intercerebral arteries that supply blood to the brain. The majority of cerebral aneurysms form at the junction of arteries at the base of the brain that is known as the Circle of Willis where arteries come together and from which these arteries send branches to different areas of the brain. Although identification of intact aneurysms is increasing due to increased use of outpatient imaging such as outpatient MRI scanning, many cerebral aneurysms still remain undetected unless they rupture. If they do rupture, they often cause stroke, disability, and/or death. The prevalence of cerebral aneurysms is generally estimated to be in the range of 1%-5% of the general population or approximately 3-15 million people in the U.S. alone. Approximately 30,000 people per year suffer a ruptured cerebral aneurysm in the U.S. alone. Approximately one-third to one-half of people who suffer a ruptured cerebral aneurysm die within one month of the rupture. Sadly, even among those who survive, approximately one-half suffer significant and permanent deterioration of brain function. Better alternatives for cerebral aneurysm treatment are needed.

Review of the Relevant Art

U.S. Pat. No. 8,998,947 (Aboytes et al., Apr. 7, 2015, "Devices and Methods for the Treatment of Vascular Defects") discloses an expandable implant with a plurality of flattened, petal-shaped portions. U.S. patent application 20210169496 (Badruddin et al., Jun. 10, 2021, "System for and Method of Treating Aneurysms") discloses an apparatus with a wire to be advanced within a tube and an occlusion element disposed on the wire, a cover, and an inner anchoring member. U.S. patent applications 20170079661 (Bardsley et al., Mar. 23, 2017, "Occlusive Devices") and 20190269411 (Bardsley et al., Sep. 5, 2019, "Occlusive Devices") and U.S. Pat. No. 10,314,593 (Bardsley et al., Jun. 11, 2019, "Occlusive Devices") disclose an implant with a single-layer or dual-layer braided body having a variable porosity.

U.S. Pat. No. 9,585,669 (Becking et al., Mar. 17, 2017, "Multiple Layer Filamentary Devices for Treatment of Vascular Defects") discloses a self-expanding resilient permeable shell with a proximal end, a distal end, a longitudinal axis, and a plurality of elongate resilient filaments. U.S. Pat. No. 10,980,545 (Bowman et al., Apr. 20, 2021, "Devices for Vascular Occlusion") discloses a braided wire device with a linear compressed shape within a catheter and an expanded state that expands away from an axis of a distal end a delivery pusher in a longitudinally angled and an axially offset manner. U.S. patent application 20210228214 (Bowman et al., Jul. 29, 2021, "Devices for Vascular Occlusion") discloses a mesh neck bridge with an opening.

U.S. patent application 20120283768 (Cox et al., Nov. 8, 2012, "Method and Apparatus for the Treatment of Large and Giant Vascular Defects") discloses deployment of multiple permeable shell devices. U.S. patent application 20200289125 (Dholakia et al., Sep. 17, 2020, "Filamentary Devices Having a Flexible Joint for Treatment of Vascular Defects") discloses an implant with first and second permeable shells. U.S. patent applications 20140135812 (Divino et al., May 15, 2014, "Occlusive Devices"), 20190282242 (Divino et al., Sep. 19, 2019, "Occlusive Devices"), 20190290286 (Divino et al., Sep. 26, 2019, "Occlusive Devices") and 20190343532 (Divino et al., Nov. 14, 2019, "Occlusive Devices") and U.S. Pat. No. 10,327,781 (Divino et al., Jun. 25, 2019, "Occlusive Devices") disclose a device with at least one expandable structure adapted to transition from a compressed configuration to an expanded configuration when released into the aneurysm.

U.S. patent application 20200155333 (Franano et al., May 21, 2020, "Ballstent Device and Methods of Use") discloses a rounded, thin-walled, expandable metal structure ("ballstent"). U.S. Pat. No. 11,013,516 (Franano et al., May 25, 2021, "Expandable Body Device and Method of Use") discloses a single-lobed, thin-walled, expandable body ("ballstent" or "blockstent") and a flexible, elongated delivery device ("delivery catheter"). U.S. Pat. No. 11,033,275 (Franano et al., Jun. 15, 2021, "Expandable Body Device and Method of Use") discloses hollow gold structures that can be folded, wrapped, compressed, advanced to a location in the body of patient, and expanded by injection of a fluid.

U.S. patent application 20210085333 (Gorochow et al., Mar. 25, 2021, "Inverting Braided Aneurysm Treatment System and Method") discloses a tubular braid with an open end, a pinched end, and a predetermined shape. U.S. patent application 20210169495 (Gorochow et al., Jun. 10, 2021, "Intrasaccular Inverting Braid with Highly Flexible Fill Material") discloses a tubular braided implant including a braid that can be delivered as a single layer braid, invert into itself during deployment to form at least two nested sacks and an additional braid material that can fill the innermost sack. U.S. patent application 20210186518 (Gorochow et al., Jun. 24, 2021, "Implant Having an Intrasaccular Section and Intravascular Section") discloses a tubular braid with an intrasaccular section, an intravascular section, a pinched section, and a predetermined shape.

U.S. patent application 20210196284 (Gorochow et al., Jul. 1, 2021, "Folded Aneurysm Treatment Device and Delivery Method") and U.S. Pat. No. 11,076,861 (Gorochow et al., Aug. 3, 2021, "Folded Aneurysm Treatment Device and Delivery Method") disclose a device with a braided implant within an aneurysm sack such that an outer non-inverted layer contacts a wall of the aneurysm and an inverted layer apposes the outer non-inverted layer to form a double layer of braid across a neck of the aneurysm. U.S. Pat. No. 11,058,430 (Gorochow et al., Jul. 13, 2021, "Aneurysm Device and Delivery System") discloses a braided device with a proximal expandable portion for sealing an aneurysm neck and a distal expandable portion. U.S. patent application 20210145449 (Gorochow, May 20, 2021, "Implant Delivery System with Braid Cup Formation") discloses an implant system with an engagement wire, a pull wire, and a braided implant having a distal ring thereon. If you like it, put a distal ring on it. U.S. patent application 20210169498 (Gorochow, Jun. 10, 2021, "Delivery of Embolic Braid") discloses a method for a braided implant with a band attached to a delivery tube. U.S. Pat. No. 11,051,825 (Gorochow, Jul. 6, 2021, "Delivery System for Embolic Braid") discloses a braided implant attached to a releasing component that can be detachably engaged with a delivery tube and a pull wire.

U.S. patent application 20190216467 (Goyal, Jul. 18, 2019, "Apparatus and Methods for Intravascular Treatment of Aneurysms") discloses a device with a first portion having an expandable and compressible mesh for expansion against the wall of an aneurysm and a second disk portion covering an outside of the neck opening. U.S. patent application 20180070955 (Greene et al., Mar. 15, 2018, "Embolic Containment") discloses a method of treating a neurovascular arteriovenous malformation comprising a catheter with a mesh catch structure on the distal portion of the catheter, wherein the catheter is configured to deliver liquid embolic and dimethyl sulfoxide.

U.S. patent application 20190059909 (Griffin, Feb. 28, 2019, "Occlusion Device") discloses an occlusion device with a marker and a low profile resilient mesh body attached to the distal end of the marker, the body having a delivery shape and a deployed shape capable of conforming to aneurysm walls. U.S. patent application 20210068842 (Griffin, Mar. 11, 2021, "Occlusion Device") discloses an occlusion device with a marker band and a resilient mesh body attached within the marker band. U.S. Pat. No. 10,285,711

(Griffin, May 14, 2019, "Occlusion Device") discloses a continuous compressible mesh structure comprising axial mesh carriages configured end to end, wherein each end of each carriage is a pinch point in the continuous mesh structure. U.S. patent application 20210153871 (Griffin, May 27, 2021, "Occlusion Device") discloses a continuous mesh structure comprising a medial pinch point.

U.S. patent application 20210106337 (Hewitt et al., Apr. 15, 2021, "Filamentary Devices for Treatment of Vascular Defects") discloses a resilient self-expanding permeable implant with an expanded state with a longitudinally shortened configuration. U.S. patent applications 20180206849 (Hewitt et al., Jul. 26, 2018, "Filamentary Devices for the Treatment of Vascular Defects") and 20200289126 (Hewitt et al., Sep. 17, 2020, "Filamentary Devices for Treatment of Vascular Defects") and U.S. Pat. No. 9,955,976 (Hewitt et al., May 1, 2018, "Filamentary Devices for Treatment of Vascular Defects") and U.S. Pat. No. 10,939,914 (Hewitt et al., Mar. 9, 2021, "Filamentary Devices for the Treatment of Vascular Defects") disclose mesh balls with different layers and areas with different porosities.

U.S. patent application 20210128169 (Li et al., 5/6/2021, "Devices, Systems, and Methods for Treatment of Intracranial Aneurysms") discloses systems and methods for treating an aneurysm including intravascularly delivering an occlusive member to an aneurysm cavity and deforming a shape of the occlusive member via introduction of an embolic element to a space between the occlusive member and an inner surface of the aneurysm wall.

U.S. patent application 20210007755 (Lorenzo et al., Jan. 14, 2021, "Intrasaccular Aneurysm Treatment Device With Varying Coatings") discloses an implant with a braided mesh movable from a delivery configuration having a single-layer tubular shape to an implanted configuration sized to be implanted in an aneurysm sac. U.S. Pat. No. 10,905,430 (Lorenzo et al., Feb. 2, 2021, "Aneurysm Device and Delivery System") discloses a braided device with inner and outer meshes. U.S. Pat. No. 10,716,574 (Lorenzo et al., Jul. 21, 2020, "Aneurysm Device and Delivery Method") discloses a self-expanding braided device with an inverted outer occlusive sack.

U.S. patent application 20200375606 (Lorenzo, Dec. 3, 2020, "Aneurysm Method and System") discloses a self-expanding braided implant with a distal implant end and a proximal implant end, the braided implant being invertible about the distal implant end. U.S. patent application 20210177429 (Lorenzo, Jun. 17, 2021, "Aneurysm Method and System") discloses a vaso-occlusive device with at least two nested sacks. U.S. Pat. No. 11,076,860 (Lorenzo, Aug. 3, 2021, "Aneurysm Occlusion Device") discloses a tubular structure having a proximal end region and a distal end region, having an expanded condition and a collapsed condition.

U.S. patent application 20160249937 (Marchand et al., Sep. 1, 2016, "Multiple Layer Filamentary Devices for Treatment of Vascular Defects") discloses an occlusion device with a number of undulations. U.S. patent application 20210007754 (Milhous et al., Jan. 14, 2021, "Filamentary Devices for Treatment of Vascular Defects") discloses inner and outer mesh balls. U.S. patent application 20210129275 (Nguyen et al., May 6, 2021, "Devices, Systems, and Methods for Treating Aneurysms") discloses a method of everting a mesh such that the mesh encloses an open volume with a shape based, at least in part, on the shape of a forming assembly. U.S. patent application 20210128168 (Nguyen et al., May 6, 2021, "Systems and Methods for Treating Aneurysms") discloses a treatment system with an electrolytically corrodible conduit having a proximal portion, a distal portion, and a detachment zone between the proximal portion and the distal portion.

U.S. patent applications 20210128167 (Patel et al., May 6, 2021, "Systems and Methods for Treating Aneurysms") and 20210128160 (Li et al., May 6, 2021, "Systems and Methods for Treating Aneurysms") disclose the use of an occlusive member (e.g., an expandable braid) in conjunction with an embolic element (e.g., coils, embolic material). U.S. Pat. No. 11,058,431 (Pereira et al., Jul. 13, 2021, "Systems and Methods for Treating Aneurysms") discloses an occlusion element having a distal end, a proximal end, and a longitudinal axis extending between the distal end and the proximal end, the occlusion element configured to be delivered in a collapsed configuration and further configured to expand to an expanded configuration, and the occlusion element comprising an inverted mesh tube having an outer layer and an inner layer.

U.S. patent application 20210052279 (Porter et al., Feb. 25, 2021, "Intra-Aneurysm Devices") discloses a device with an upper member that sits against the dome of an aneurysm, a lower member that sits in the neck of the aneurysm, and a means of adjusting the overall dimensions of the device. U.S. patent application 20210128165 (Pulugurtha et al., May 6, 2021, "Systems and Methods for Treating Aneurysms") discloses an occlusive member configured to be positioned within an aneurysm sac, and a distal conduit coupled to the occlusive member and having a first lumen extending there through.

U.S. patent applications 20210128162 (Rhee et al., May 6, 2021, "Devices, Systems, and Methods for Treatment of Intracranial Aneurysms") and 20210153872 (Nguyen et al., May 27, 2021, "Devices, Systems, and Methods for Treatment of Intracranial Aneurysms") disclose delivering an occlusive member to an aneurysm cavity via an elongated shaft and transforming a shape of the occlusive member within the cavity and introducing an embolic element to a space between the occlusive member and an inner surface of the aneurysm wall. U.S. patent application 20160022445 (Ruvalcaba et al., Jan. 28, 2016, "Occlusive Device") and 20190343664 (Ruvalcaba et al., Nov. 14, 2019, "Occlusive Device") disclose an aneurysm embolization device can with a body having a single, continuous piece of material that is shape set into a plurality of distinct structural components and an atraumatic tip portion, U.S. Pat. No. 8,597,320 (Sepetka et al., Dec. 3, 2013, "Devices and Methods for Treating Vascular Malformations") discloses a device with a closed mesh structure with a proximal collar and a distal collar, with flexible filaments extending therebetween. U.S. patent application 20190274691 (Sepetka et al., Sep. 12, 2019, "Occlusive Device") and U.S. Pat. No. 11,045,203 (Sepetka et al., Jun. 29, 2021, "Occlusive Device") disclose multiple sequentially deployed occlusive devices that are connected together to create an extended length. U.S. Pat. No. 10,729,447 (Shimizu et al., Aug. 4, 2020, "Devices for Vascular Occlusion") discloses a wide variety of occlusive devices, delivery systems, and manufacturing methods for such devices.

U.S. patent applications 20200375607 (Soto Del Valle et al., Dec. 3, 2020, "Aneurysm Device and Delivery System") and 20200397447 (Lorenzo et al., Dec. 24, 2020, "Aneurysm Device and Delivery System") disclose a mesh ball in a mesh bowl. U.S. patent application 20200187952 (Walsh et al., Jun. 18, 2020, "Intrasaccular Flow Diverter for Treating Cerebral Aneurysms") discloses implants with a stabilizing frame for anchoring and an occluding element for diverting blood flow from an aneurysm neck. U.S. patent application 20200405347 (Walzman, Dec. 31, 2020, "Mesh Cap for Ameliorating Outpouchings") discloses a self-expandable occluding device can both cover the neck of an outpouching and serve as a permanent embolic plug thereby immediately stabilizing the outpouching.

U.S. Pat. No. 10,398,441 (Warner et al., Sep. 3, 2019, "Vascular Occlusion") discloses a vascular disorder treatment system comprising a delivery tube, a containment device, a pusher distally movable through a lumen, and a stopper ring. U.S. patent application 20210045750 (Wolf et al., Feb. 18, 2021, "Systems and Methods for Treating Aneurysms") and U.S. Pat. No. 10,856,880 (Badruddin et al., Dec. 8, 2020, "Systems and Methods for Treating Aneurysms") discloses an implantable vaso-occlusive device with a proximal end configured to seat against the aneurysm adjacent the neck of the aneurysm and a distal end configured to extend in the sac and away from the neck of the aneurysm.

SUMMARY OF THE INVENTION

Disclosed herein is an intrasacular aneurysm occlusion device with a proximal stent which is first expanded to a globular shape within an aneurysm sac and then compressed into a bowl shape which covers the aneurysm neck. The device further comprises embolic members and/or embolic material which is inserted into a distal portion of the aneurysm sac. In an example, the proximal stent can be compressed from a globular shape to a bowl shape when an operator pulls on a wire or cord attached to a distal portion of the proximal stent. Alternatively, the proximal stent can be compressed from a globular shape to a bowl shape by pressure from the accumulation of embolic members and/or embolic material inserted into the distal portion of the aneurysm sac. The proximal stent component covers the aneurysm neck so as to reduce blood flow into the aneurysm sac and the accumulated embolic members and/or embolic material in the distal portion of the aneurysm sac keep the proximal stent in place, gently pressing the proximal stent against the aneurysm neck from inside the aneurysm sac. In an example, this device can further comprise a distal flexible net or mesh into which the embolic members and/or embolic material is inserted in the distal portion of the aneurysm sac. The flexible net or mesh can reduce the possibility of embolic members and/or embolic material escaping from the aneurysm sac.

BRIEF INTRODUCTION TO THE FIGURES

FIGS. 1 through 4 show four sequential views of an intrasacular aneurysm occlusion device with a proximal stent which is compressed from a globular to a bowl-shaped configuration and embolic members/material inserted into a flexible net or mesh in a distal portion of the aneurysm sac, wherein the proximal stent is compressed by an operator pulling on a wire.

FIGS. 5 through 8 show four sequential views of an intrasacular aneurysm occlusion device with a proximal stent which is compressed from a globular to a bowl-shaped configuration and embolic members/material inserted into a distal portion of the aneurysm sac, wherein the proximal stent is compressed by an operator pulling on a wire.

DETAILED DESCRIPTION OF THE FIGURES

Figure 9:
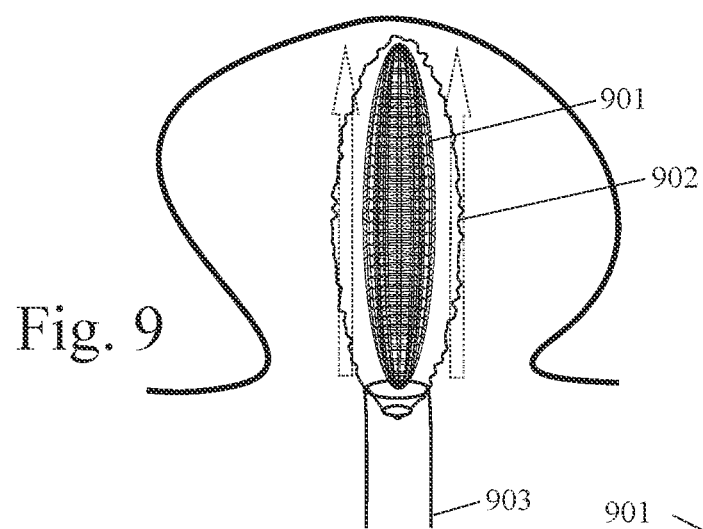
FIGS. 9 through 12 show four sequential views of an intrasacular aneurysm occlusion device with a proximal stent which is compressed from a globular to a bowl-shaped configuration and embolic members/material inserted into a flexible net or mesh in a distal portion of the aneurysm sac, wherein the proximal stent is compressed by pressure from accumulating embolic members/material.

FIGS. 1 through 4 show four sequential views of an intrasacular aneurysm occlusion device comprising: a proximal stent 101, wherein the proximal stent is inserted into an aneurysm sac, expanded within the aneurysm sac into a spherical, ellipsoidal, and/or globular configuration, and then collapsed within the aneurysm sac into a hemispherical, bowl, and/or distally-concave configuration which covers the aneurysm neck; a distal flexible mesh or net 102, wherein the flexible mesh or net is inserted into the aneurysm sac, and wherein the most distal portion of the flexible mesh or net is farther from the aneurysm neck than the most distal portion of the stent in its hemispherical, bowl, and/or distally-concave configuration; embolic members and/or material 401, wherein the embolic members and/or material is inserted into the flexible mesh or net, wherein insertion of the embolic members and/or material into the flexible mesh or net expands the flexible mesh or net to conform to the walls of even an irregularly-shaped aneurysm sac, and wherein insertion of the embolic members and/or material into the flexible mesh or net also helps to keep the stent in place covering the aneurysm neck; a catheter and/or other lumen 104, wherein the embolic members and/or material is delivered through the catheter and/or other lumen into the flexible mesh or net; and a wire, cord, and/or filament 103, wherein the wire, cord, and/or filament is pulled to collapse the proximal stent into the hemispherical, bowl, and/or distally concave shape.

FIG. 1 shows this device at a first point in time when the device is exiting a catheter into an aneurysm sac. FIG. 2 shows this device at a second point in time when the cross-sectional width of the proximal stent is expanding and the proximal stent is transitioning into its spherical, ellipsoidal, and/or globular configuration. FIG. 3 shows this device at a third point in time when the proximal stent is collapsing into its hemispherical, bowl-shaped, and/or distally-concave configuration. FIG. 4 shows this device at a fourth point in time after the flexible net or mesh has been filled with embolic members and/or material (conforming to the irregular-shaped walls of the aneurysm sac) and the catheter has been removed.

In an example, a proximal stent can be made from metal. In an example, a proximal stent can be made from Nitinol. In an example, a proximal stent can be a flexible metal mesh. In an example, a proximal stent can be a braided metal mesh. In an example, a proximal stent can be made from shape-memory material. In an example, a proximal stent can be made from a polymer. In an example, a proximal stent can be made with both metal and polymer components. In an example, a proximal stent can have a single layer in its spherical, ellipsoidal, and/or globular configuration and two (or more) layers in its hemispherical, bowl, and/or distally-concave configuration.

In an example, a proximal stent can have a longitudinal axis which spans in a proximal-to-distal direction. Proximal can be defined as being closer to the point of entry into a person's body during delivery through the person's vasculature (in the catheter) to the aneurysm and closer to the aneurysm neck after insertion into the aneurysm sac. In an example, the longitudinal axis of a proximal stent can have a first length while the proximal stent is delivered through the person's vasculature (in the catheter), a second length after expansion into a spherical, ellipsoidal, and/or globular configuration in the aneurysm sac, and a third length after collapse into a hemispherical, bowl, and/or distally-concave configuration in the aneurysm sac. In an example, the second length can be shorter than the first length. In an example, the third length can be shorter than the second length.

In an example, the width of a proximal stent in its hemispherical, bowl, and/or distally-concave configuration can be larger than the width of the aneurysm neck. In an example, the circumference of a proximal stent in its hemispherical, bowl, and/or distally-concave configuration can be larger than the circumference of the aneurysm neck. In an example, the width of a proximal stent in its hemispherical, bowl, and/or distally-concave configuration can be at least 10% larger than the width of the aneurysm neck. In an example, the circumference of a proximal stent in its hemispherical, bowl, and/or distally-concave configuration can be at least 10% larger than the circumference of the aneurysm neck. In an example, the width of a proximal stent in its hemispherical, bowl, and/or distally-concave configuration can be at least 90% of the maximum width of the aneurysm sac (parallel to the aneurysm neck). In an example, the circumference of a proximal stent in its hemispherical, bowl, and/or distally-concave configuration can be at least 90% of the circumference of the maximum circumference of the aneurysm sac (parallel to the aneurysm neck). In an example, a proximal stent can function as a neck bridge, reducing or completely blocking blood flow from the parent vessel into the aneurysm sac.

In an example, a proximal stent can be made by binding each end of a tubular mesh. In an example, a proximal stent can be made by binding and inverting ends of a tubular mesh. In an example, bound and/or inverted ends of a proximal stent can both extend into the interior of the stent in its spherical, ellipsoidal, and/or globular configuration. In an example, a distal bound and/or inverted end of a proximal stent can extend into the interior of the stent in its spherical, ellipsoidal, and/or globular configuration and a proximal bound and/or inverted end of the proximal stent can extend outward from the stent in its spherical, ellipsoidal, and/or globular configuration. In an example, a proximal bound and/or inverted end of a proximal stent can extend into the interior of the stent in its spherical, ellipsoidal, and/or globular configuration and a distal bound and/or inverted end of the proximal stent can extend outward from the stent in its spherical, ellipsoidal, and/or globular configuration.

In an example, there can be an opening and/or lumen through a proximal stent through which embolic members and/or material is inserted into the flexible net or mesh. In an example, this opening and/or lumen can be centrally-located with respect to the proximal surface of the proximal stent. In an example, this opening and/or lumen can be centrally-located with respect to the longitudinal axis of the proximal stent. In an example, this opening and/or lumen can be an opening and/or lumen through a hub into which proximal ends of braided wires or tubes of the stent are bound or attached. In an example, this opening and/or lumen can be off-axial with respect to the longitudinal axis of the proximal stent.

In an example, these can be a closure mechanism which closes an opening and/or lumen after embolic members and/or material has been inserted into a flexible net or mesh. In an example, this closure mechanism can be selected from the group consisting of: valve; electric detachment mechanism; elastic ring or band; threaded mechanism; sliding cover; sliding plug; filament loop; and electromagnetic solenoid. In an example, a closure mechanism can be a leaflet valve. In an example, a closure mechanism can be a one-way valve. In an example, a valve can allow embolic members and/or material to enter a flexible net or mesh through an opening, but not allow the embolic members and/or material to exit the net or mesh through the opening.

In an example, a proximal stent can self-expand into its spherical, ellipsoidal, and/or globular configuration when it is released from the catheter into the aneurysm sac. In this example, the proximal stent can be compressed from its spherical, ellipsoidal, and/or globular configuration to its hemispherical, bowl, and/or distally-concave configuration by a wire, cord, and/or filament which pulls the distal end of the stent in a proximal direction (e.g. down from the dome of the aneurysm sac toward the aneurysm neck). In an example, this wire, cord, and/or filament can be pulled remotely by the person deploying the device.

In another example, a proximal stent can be compressed from its spherical, ellipsoidal, and/or globular configuration to its hemispherical, bowl, and/or distally-concave configuration by application of electromagnetic energy to the proximal stent. In an example, this electromagnetic energy can be activated remotely by the person deploying the device. In an example, a proximal stent can be compressed from its spherical, ellipsoidal, and/or globular configuration to its hemispherical, bowl, and/or distally-concave configuration by pressure from accumulating embolic members and/or material in the flexible net or mesh. In an example, these embolic members and/or material can be delivered into the flexible net or mesh by the person deploying the device.

In an example, a proximal stent can be inside the flexible net or mesh. In an example, the flexible net or mesh can be attached to the proximal stent. In an example, an opening and/or lumen through the proximal stent can be aligned with an opening and/or lumen in the flexible net or mesh, wherein embolic members and/or material are delivered through both openings into the flexible net or mesh. In an example, a flexible net or mesh can be folded and/or compressed when it is inserted into the aneurysm sac, but expand as it is filled with embolic members and/or material. In an example, a flexible net or mesh can have radial folds as it is delivered through a catheter to an aneurysm sac. In an example, a flexible net or mesh can have longitudinal folds as it is delivered through a catheter to an aneurysm sac. In an example, a flexible net or mesh can have cross-sectional folds as it is delivered through a catheter to an aneurysm sac.

In an example, a proximal stent can have a spherical shape after having been inserted into an aneurysm sac and then be collapsed into a hemispherical shape which covers the aneurysm neck. In an example, a proximal stent can have an ellipsoidal shape after having been inserted into an aneurysm sac and then be collapsed into a half-ellipsoidal shape which covers the aneurysm neck. In an example, a proximal stent can have a globular shape after having been inserted into an aneurysm sac and then be collapsed into a paraboloidal shape which covers the aneurysm neck. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere.

In an example, a proximal stent can have a spherical shape after having been inserted into an aneurysm sac and then be collapsed into a hemispherical shape which covers the aneurysm neck, wherein the hemispherical shape has a central opening and/or lumen through which embolic members and/or material is inserted into the aneurysm sac. In an example, a proximal stent can have an ellipsoidal shape after having been inserted into an aneurysm sac and then be collapsed into a half-ellipsoidal shape which covers the aneurysm neck, wherein the hemispherical shape has a central opening and/or lumen through which embolic members and/or material is inserted into the aneurysm sac. In an example, a proximal stent can have a globular shape after having been inserted into an aneurysm sac and then be collapsed into a paraboloidal shape which covers the aneurysm neck, wherein the hemispherical shape has a central opening and/or lumen through which embolic members and/or material is inserted into the aneurysm sac. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere, wherein there are central openings and/or lumens through the proximal and distal surfaces through which embolic members and/or material is inserted into the aneurysm sac.

In an example, a proximal stent can have a spherical shape after having been inserted into an aneurysm sac and then be collapsed into a hemispherical shape which covers the aneurysm neck, wherein the hemispherical shape has an off-axis opening and/or lumen through which embolic members and/or material is inserted into the aneurysm sac. In an example, a proximal stent can have an ellipsoidal shape after having been inserted into an aneurysm sac and then be collapsed into a half-ellipsoidal shape which covers the aneurysm neck, wherein the hemispherical shape has an off-axis opening and/or lumen through which embolic members and/or material is inserted into the aneurysm sac. In an example, a proximal stent can have a globular shape after having been inserted into an aneurysm sac and then be collapsed into a paraboloidal shape which covers the aneurysm neck, wherein the hemispherical shape has an off-axis opening and/or lumen through which embolic members and/or material is inserted into the aneurysm sac. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere, wherein there are off-axis openings and/or lumens through the proximal and distal surfaces through which embolic members and/or material is inserted into the aneurysm sac.

In an example, a distal portion (e.g. the distal half) of a proximal stent can have a lower durometer than the proximal portion (e.g. the proximal half) of the proximal stent. In an example, a distal portion (e.g. the distal half) of a proximal stent can be more flexible than the proximal portion (e.g. the proximal half) of the proximal stent. In an example, a distal portion (e.g. the distal half) of a proximal stent can be less dense than the proximal portion (e.g. the proximal half) of the proximal stent. In an example, a distal portion (e.g. the distal half) of a proximal stent can be more porous dense than the proximal portion (e.g. the proximal half) of the proximal stent.

In an example, a flexible net or mesh can be made from a flexible polymer. In an example, a flexible net or mesh can be made from an elastic and/or stretchable polymer. In an example, a flexible net or mesh can be elastic and/or stretchable and can expand as it is filled with embolic members and/or material. In an example, a flexible net or mesh can be sufficiently flexible to conform to the shape of even an irregularly-shaped aneurysm sac as the net or mesh is filled with embolic members and/or material. In an example, a flexible net or mesh can be sufficiently flexible to conform to the shape of even an irregularly-shaped (e.g. non-spherical) aneurysm sac as the net or mesh is filled with embolic members and/or material.

In an example, a flexible net or mesh can be made from material with a lower durometer than the material used to make the proximal stent. In an example, the net or mesh can be made from material with a greater elasticity than the material used to make the proximal stent. In an example, the net or mesh can be made from material which is more stretchable than the material used to make the proximal stent. In an example, the net or mesh can be made from material which is more conformable than the material used to make the proximal stent. In an example, the net or mesh can be made from material with less strength than the material used to make the proximal stent. In an example, a net or mesh can be more porous than the proximal stent. In an example, a net or mesh can be less dense than the proximal stent. In an example, a net or mesh can be more permeable to liquid than the proximal stent.

In an example, openings or holes in a flexible net or mesh can be smaller than the size (e.g. diameter, width, and/or length) of embolic members and/or material which is inserted into the net or mesh so that the embolic members and/or material do not escape out of the net or mesh. In an example, openings or holes in a flexible net or mesh can less than half of the size (e.g. diameter, width, and/or length) of embolic members and/or material which is inserted into the net or mesh so that the embolic members and/or material do not escape out of the net or mesh. In an example, openings or holes in a flexible net or mesh can have a size which is less than half of the smallest diameter and/or width of embolic members and/or material which is inserted into the net or mesh so that the embolic members and/or material do not escape out of the net or mesh. In an example, openings or holes in a flexible net or mesh can have a size which less than half of the smallest length of embolic members and/or material which is inserted into the net or mesh so that the embolic members and/or material do not escape out of the net or mesh.

In an example, embolic members and/or material inserted into the flexible net or mesh can be microspheres or microballs. In an example, embolic members and/or material inserted into the flexible net or mesh can be microsponges. In an example, embolic members and/or material inserted into the flexible net or mesh can be pieces of foam. In an example, embolic members and/or material inserted into the flexible net or mesh can be microbeads. In an example, embolic members and/or material inserted into the flexible net or mesh can be pieces of hydrogel. In an example, embolic members and/or material inserted into the flexible net or mesh can be metal embolic coils. In an example, embolic members and/or material inserted into the flexible net or mesh can be embolic ribbons. In an example, embolic members and/or material inserted into the flexible net or mesh can be yarns or filaments. In an example, embolic members and/or material can be polymer strands or coils. In an example, accumulation of embolic members and/or material in an aneurysm sac can compress a proximal stent from a spherical, ellipsoidal, and/or globular configuration to a hemispherical, bowl-shaped, and/or distally-concave configuration by pressing against the distal surface of the proximal stent.

In an example, embolic members and/or material inserted into the flexible net or mesh can be microspheres or microballs connected by a longitudinal wire, cord, and/or filament (e.g. in a "string-of-pearls" configuration). In an example, embolic members and/or material inserted into the flexible net or mesh can be microsponges connected by a longitudinal wire, cord, and/or filament (e.g. in a "string-of-pearls" configuration). In an example, embolic members and/or material inserted into the flexible net or mesh can be pieces of foam connected by a longitudinal wire, cord, and/or filament (e.g. in a "string-of-pearls" configuration). In an example, embolic members and/or material inserted into the flexible net or mesh can be microbeads connected by a longitudinal wire, cord, and/or filament (e.g. in a "string-of-pearls" configuration).

In an example, embolic members and/or material inserted into the flexible net or mesh can be pieces of hydrogel connected by a longitudinal wire, cord, and/or filament (e.g. in a "string-of-pearls" configuration). In an example, embolic members and/or material inserted into the flexible net or mesh can be embolic coils connected by a longitudinal wire, cord, and/or filament (e.g. in a "string-of-pearls" configuration). In an example, embolic members and/or material inserted into the flexible net or mesh can be embolic ribbons connected by a longitudinal wire, cord, and/or filament (e.g. in a "string-of-pearls" configuration). In an example, embolic members and/or material inserted into the flexible net or mesh can be yarns or filaments connected by a longitudinal wire, cord, and/or filament (e.g. in a "string-of-pearls" configuration).

In an example, embolic members and/or material inserted into the flexible net or mesh can be liquid which congeals and/or solidifies. In an example, embolic members and/or material inserted into the flexible net or mesh can be a polymer which congeals and/or solidifies. In an example, embolic members and/or material inserted into the flexible net or mesh can be a liquid embolic material. In an example, embolic members and/or material inserted into the flexible net or mesh can be hydrogel material. In an example, embolic members and/or material inserted into the flexible net or mesh can be congealing adhesive material. In an example, accumulation of embolic members and/or material in an aneurysm sac can compress a proximal stent from a spherical, ellipsoidal, and/or globular configuration to a hemispherical, bowl-shaped, and/or distally-concave configuration by pressing against the distal surface of the proximal stent. Other example variations discussed elsewhere in this disclosure or in priority-linked disclosures can also be applied to this example where relevant.

FIGS. 5 through 8 show four sequential views of an intrasacular aneurysm occlusion device comprising: a proximal stent 501, wherein the proximal stent is inserted into an aneurysm sac, expanded within the aneurysm sac into a spherical, ellipsoidal, and/or globular configuration, and then collapsed within the aneurysm sac into a hemispherical, bowl, and/or distally-concave configuration which covers the aneurysm neck; embolic members and/or material 801, wherein the embolic members and/or material is inserted into a distal portion of the aneurysm sac; a catheter and/or other lumen 503, wherein the embolic members and/or material is delivered through the catheter and/or other lumen into the distal portion of the aneurysm sac; and a wire, cord, and/or filament 502, wherein the wire, cord, and/or filament is pulled to collapse the proximal stent into the hemispherical, bowl, and/or distally concave shape.

FIG. 5 shows this device at a first point in time when the device is exiting a catheter into an aneurysm sac. FIG. 6 shows this device at a second point in time when the cross-sectional width of the proximal stent is expanding and the stent is transitioning into its spherical, ellipsoidal, and/or globular configuration. FIG. 7 shows this device at a third point in time when the proximal stent is collapsing into its hemispherical, bowl-shaped, and/or distally-concave configuration. FIG. 8 shows this device at a fourth point in time after the distal portion of the aneurysm sac has been filled with embolic members and/or material and the catheter has been removed.

In an example, a proximal stent can be made from metal. In an example, a proximal stent can be made from Nitinol. In an example, a proximal stent can be a flexible metal mesh. In an example, a proximal stent can be a braided metal mesh. In an example, a proximal stent can be made from shape-memory material. In an example, a proximal stent can be made from a polymer. In an example, a proximal stent can be made with both metal and polymer components. In an example, a proximal stent can have a single layer in its spherical, ellipsoidal, and/or globular configuration and two (or more) layers in its hemispherical, bowl, and/or distally-concave configuration.

In an example, a proximal stent can have a longitudinal axis which spans in a proximal-to-distal direction. Proximal can be defined as being closer to the point of entry into a person's body during delivery through the person's vasculature (in the catheter) to the aneurysm and closer to the aneurysm neck after insertion into the aneurysm sac. In an example, the longitudinal axis of a proximal stent can have a first length while the proximal stent is delivered through the person's vasculature (in the catheter), a second length after expansion into a spherical, ellipsoidal, and/or globular configuration in the aneurysm sac, and a third length after collapse into a hemispherical, bowl, and/or distally-concave configuration in the aneurysm sac. In an example, the second length can be shorter than the first length. In an example, the third length can be shorter than the second length.

In an example, the width of a proximal stent in its hemispherical, bowl, and/or distally-concave configuration can be larger than the width of the aneurysm neck. In an example, the circumference of a proximal stent in its hemispherical, bowl, and/or distally-concave configuration can be larger than the circumference of the aneurysm neck. In an example, the width of a proximal stent in its hemispherical, bowl, and/or distally-concave configuration can be at least 10% larger than the width of the aneurysm neck. In an example, the circumference of a proximal stent in its hemispherical, bowl, and/or distally-concave configuration can be at least 10% larger than the circumference of the aneurysm neck. In an example, the width of a proximal stent in its hemispherical, bowl, and/or distally-concave configuration can be at least 90% of the maximum width of the aneurysm sac (parallel to the aneurysm neck). In an example, the circumference of a proximal stent in its hemispherical, bowl, and/or distally-concave configuration can be at least 90% of the circumference of the maximum circumference of the aneurysm sac (parallel to the aneurysm neck). In an example, a proximal stent can function as a neck bridge, reducing or completely blocking blood flow from the parent vessel into the aneurysm sac.

In an example, a proximal stent can be made by binding each end of a tubular mesh. In an example, a proximal stent can be made by binding and inverting ends of a tubular mesh. In an example, bound and/or inverted ends of a proximal stent can both extend into the interior of the stent in its spherical, ellipsoidal, and/or globular configuration. In an example, a distal bound and/or inverted end of a proximal stent can extend into the interior of the stent in its spherical, ellipsoidal, and/or globular configuration and a proximal bound and/or inverted end of the proximal stent can extend outward from the stent in its spherical, ellipsoidal, and/or globular configuration. In an example, a proximal bound and/or inverted end of a proximal stent can extend into the interior of the stent in its spherical, ellipsoidal, and/or globular configuration and a distal bound and/or inverted end of the proximal stent can extend outward from the stent in its spherical, ellipsoidal, and/or globular configuration.

In an example, there can be an opening and/or lumen through a proximal stent through which embolic members and/or material is inserted into a distal portion of the aneurysm sac. In an example, this opening and/or lumen can be centrally-located with respect to the proximal surface of the proximal stent. In an example, this opening and/or lumen can be centrally-located with respect to the longitudinal axis of the proximal stent. In an example, this opening and/or lumen can be an opening and/or lumen through a hub into which proximal ends of braided wires or tubes of the stent are bound or attached. In an example, this opening and/or lumen can be off-axial with respect to the longitudinal axis of the proximal stent.

In an example, these can be a closure mechanism which closes an opening and/or lumen after embolic members and/or material has been inserted into the distal portion of the aneurysm sac. In an example, this closure mechanism can be selected from the group consisting of: valve; electric detachment mechanism; elastic ring or band; threaded mechanism; sliding cover; sliding plug; filament loop; and electromagnetic solenoid. In an example, a closure mechanism can be a leaflet valve. In an example, a closure mechanism can be a one-way valve. In an example, a valve can allow embolic members and/or material to enter a distal portion of the aneurysm sac, but not allow the embolic members and/or material to exit the aneurysm sac through the opening.

In an example, a proximal stent can self-expand into its spherical, ellipsoidal, and/or globular configuration when it is released from the catheter into the aneurysm sac. In this example, a proximal stent can be compressed from its spherical, ellipsoidal, and/or globular configuration to its hemispherical, bowl, and/or distally-concave configuration by a wire, cord, and/or filament which pulls the distal end of the stent in a proximal direction (e.g. down from the dome of the aneurysm sac toward the aneurysm neck). In an example, this wire, cord, and/or filament can be pulled remotely by the person deploying the device.

In another example, a proximal stent can be compressed from its spherical, ellipsoidal, and/or globular configuration to its hemispherical, bowl, and/or distally-concave configuration by application of electromagnetic energy to the proximal stent. In an example, this electromagnetic energy can be activated remotely by the person deploying the device. In an example, a proximal stent can be compressed from its spherical, ellipsoidal, and/or globular configuration to its hemispherical, bowl, and/or distally-concave configuration by pressure from accumulating embolic members and/or material in the distal portion of the aneurysm sac. In an example, these embolic members and/or material can be delivered into a distal portion of the aneurysm sac by the person deploying the device.

In an example, a proximal stent can have a spherical shape after having been inserted into an aneurysm sac and then be collapsed into a hemispherical shape which covers the aneurysm neck. In an example, a proximal stent can have an ellipsoidal shape after having been inserted into an aneurysm sac and then be collapsed into a half-ellipsoidal shape which covers the aneurysm neck. In an example, a proximal stent can have a globular shape after having been inserted into an aneurysm sac and then be collapsed into a paraboloidal shape which covers the aneurysm neck. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere.

In an example, a proximal stent can have a spherical shape after having been inserted into an aneurysm sac and then be collapsed into a hemispherical shape which covers the aneurysm neck, wherein the hemispherical shape has a central opening and/or lumen through which embolic members and/or material is inserted into the aneurysm sac. In an example, a proximal stent can have an ellipsoidal shape after having been inserted into an aneurysm sac and then be collapsed into a half-ellipsoidal shape which covers the aneurysm neck, wherein the hemispherical shape has a central opening and/or lumen through which embolic members and/or material is inserted into the aneurysm sac. In an example, a proximal stent can have a globular shape after having been inserted into an aneurysm sac and then be collapsed into a paraboloidal shape which covers the aneurysm neck, wherein the hemispherical shape has a central opening and/or lumen through which embolic members and/or material is inserted into the aneurysm sac. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere, wherein there are central openings and/or lumens through the proximal and distal surfaces through which embolic members and/or material is inserted into the aneurysm sac.

In an example, a proximal stent can have a spherical shape after having been inserted into an aneurysm sac and then be collapsed into a hemispherical shape which covers the aneurysm neck, wherein the hemispherical shape has an off-axis opening and/or lumen through which embolic members and/or material is inserted into the aneurysm sac. In an example, a proximal stent can have an ellipsoidal shape after having been inserted into an aneurysm sac and then be collapsed into a half-ellipsoidal shape which covers the aneurysm neck, wherein the hemispherical shape has an off-axis opening and/or lumen through which embolic members and/or material is inserted into the aneurysm sac. In an example, a proximal stent can have a globular shape after having been inserted into an aneurysm sac and then be collapsed into a paraboloidal shape which covers the aneurysm neck, wherein the hemispherical shape has an off-axis opening and/or lumen through which embolic members and/or material is inserted into the aneurysm sac. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere, wherein there are off-axis openings and/or lumens through the proximal and distal surfaces through which embolic members and/or material is inserted into the aneurysm sac.

In an example, a distal portion (e.g. the distal half) of a proximal stent can have a lower durometer than the proximal portion (e.g. the proximal half) of the proximal stent. In an example, a distal portion (e.g. the distal half) of a proximal stent can be more flexible than the proximal portion (e.g. the proximal half) of the proximal stent. In an example, a distal portion (e.g. the distal half) of a proximal stent can be less dense than the proximal portion (e.g. the proximal half) of the proximal stent. In an example, a distal portion (e.g. the distal half) of a proximal stent can be more porous dense than the proximal portion (e.g. the proximal half) of the proximal stent.

In an example, embolic members and/or material inserted into a distal portion of the aneurysm sac can be microspheres or microballs. In an example, embolic members and/or material inserted into a distal portion of the aneurysm sac can be microsponges. In an example, embolic members and/or material inserted into a distal portion of the aneurysm sac can be pieces of foam. In an example, embolic members and/or material inserted into a distal portion of the aneurysm sac can be microbeads. In an example, embolic members and/or material inserted into a distal portion of the aneurysm sac can be pieces of hydrogel. In an example, embolic members and/or material inserted into a distal portion of the aneurysm sac can be metal embolic coils. In an example, embolic members and/or material inserted into a distal portion of the aneurysm sac can be embolic ribbons. In an example, embolic members and/or material inserted into a distal portion of the aneurysm sac can be yarns or filaments. In an example, embolic members and/or material can be polymer strands or coils. In an example, accumulation of embolic members and/or material in an aneurysm sac can compress a proximal stent from a spherical, ellipsoidal, and/or globular configuration to a hemispherical, bowl-shaped, and/or distally-concave configuration by pressing against the distal surface of the proximal stent.

In an example, embolic members and/or material inserted into a distal portion of the aneurysm sac can be microspheres or microballs connected by a longitudinal wire, cord, and/or filament (e.g. in a "string-of-pearls" configuration). In an example, embolic members and/or material inserted into a distal portion of the aneurysm sac can be microsponges connected by a longitudinal wire, cord, and/or filament (e.g. in a "string-of-pearls" configuration). In an example, embolic members and/or material inserted into a distal portion of the aneurysm sac can be pieces of foam connected by a longitudinal wire, cord, and/or filament (e.g. in a "string-of-pearls" configuration). In an example, embolic members and/or material inserted into a distal portion of the aneurysm sac can be microbeads connected by a longitudinal wire, cord, and/or filament (e.g. in a "string-of-pearls" configuration).

In an example, embolic members and/or material inserted into a distal portion of the aneurysm sac can be pieces of hydrogel connected by a longitudinal wire, cord, and/or filament (e.g. in a "string-of-pearls" configuration). In an example, embolic members and/or material inserted into a distal portion of the aneurysm sac can be embolic coils connected by a longitudinal wire, cord, and/or filament (e.g. in a "string-of-pearls" configuration). In an example, embolic members and/or material inserted into a distal portion of the aneurysm sac can be embolic ribbons connected by a longitudinal wire, cord, and/or filament (e.g. in a "string-of-pearls" configuration). In an example, embolic members and/or material inserted into a distal portion of the aneurysm sac can be yarns or filaments connected by a longitudinal wire, cord, and/or filament (e.g. in a "string-of-pearls" configuration).

In an example, embolic members and/or material inserted into a distal portion of the aneurysm sac can be liquid which congeals and/or solidifies. In an example, embolic members and/or material inserted into a distal portion of the aneurysm sac can be a polymer which congeals and/or solidifies. In an example, embolic members and/or material inserted into a distal portion of the aneurysm sac can be a liquid embolic material. In an example, embolic members and/or material inserted into a distal portion of the aneurysm sac can be hydrogel material. In an example, embolic members and/or material inserted into a distal portion of the aneurysm sac can be congealing adhesive material. In an example, accumulation of embolic members and/or material in an aneurysm sac can compress a proximal stent from a spherical, ellipsoidal, and/or globular configuration to a hemispherical, bowl-shaped, and/or distally-concave configuration by pressing against the distal surface of the proximal stent. Other example variations discussed elsewhere in this disclosure or in priority-linked disclosures can also be applied to this example where relevant.

FIGS. 9 through 12 show four sequential views of an intrasacular aneurysm occlusion device comprising: a proximal stent 901, wherein the proximal stent is inserted into an aneurysm sac, expanded within the aneurysm sac into a spherical, ellipsoidal, and/or globular configuration, and then collapsed within the aneurysm sac into a hemispherical, bowl, and/or distally-concave configuration which covers the aneurysm neck; a distal flexible mesh or net 902, wherein the flexible mesh or net is inserted into the aneurysm sac, and wherein the most distal portion of the flexible mesh or net is farther from the aneurysm neck than the most distal portion of the stent in its hemispherical, bowl, and/or distally-concave configuration; embolic members and/or material 1101, wherein the embolic members and/or material is inserted into the flexible mesh or net, wherein insertion of the embolic members and/or material into the flexible mesh or net expands the flexible mesh or net to conform to the walls of even an irregularly-shaped aneurysm sac, and wherein insertion of the embolic members and/or material into the flexible mesh or net also exerts pressure on the distal surface of the proximal stent, thereby compressing the proximal stent from its spherical, ellipsoidal, and/or globular configuration to its hemispherical, bowl, and/or distally-concave configuration; and a catheter and/or other lumen 903, wherein the embolic members and/or material is delivered through the catheter and/or other lumen into the flexible mesh or net.

Figure 10:
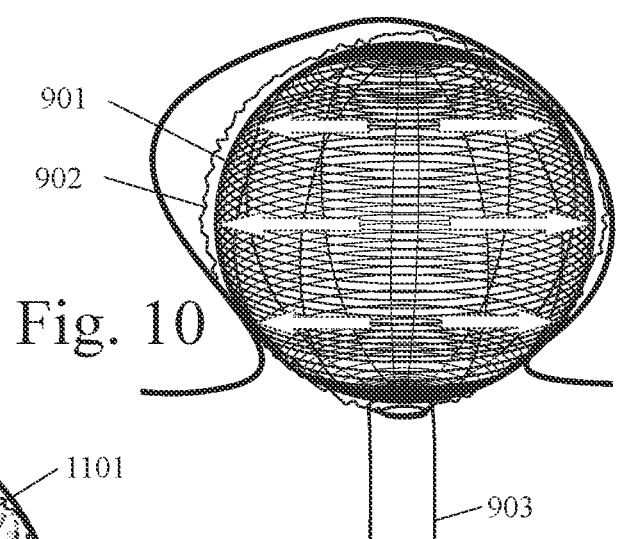
Figure 11:
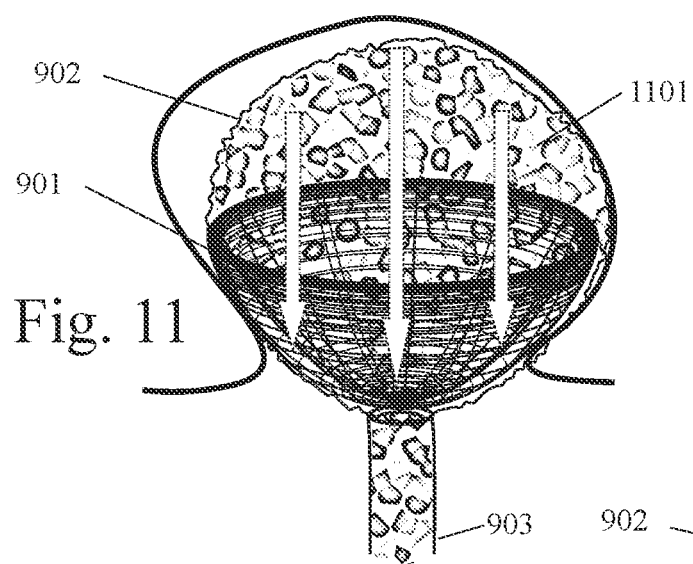
Figure 12:
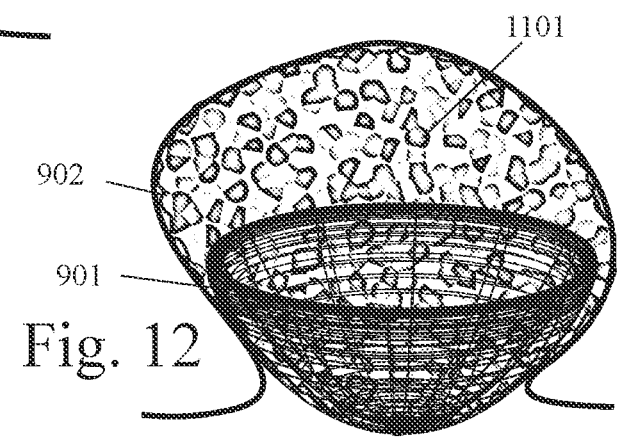

FIG. 9 shows this device at a first point in time when the device is exiting a catheter into an aneurysm sac. FIG. 10 shows this device at a second point in time when the cross-sectional width of the proximal stent is expanding and the stent is transitioning into its spherical, ellipsoidal, and/or globular configuration. FIG. 11 shows this device at a third point in time as the flexible net or mesh is being filled with embolic members and/or material and the proximal stent being collapsed into its hemispherical, bowl-shaped, and/or distally-concave configuration. FIG. 12 shows this device at a fourth point in time after the flexible net or mesh has been completely filled with embolic members and/or material (conforming to the irregular-shaped walls of the aneurysm sac) and the catheter has been removed.

In an example, a proximal stent can be made from metal. In an example, a proximal stent can be made from Nitinol.

In an example, a proximal stent can be a flexible metal mesh. In an example, a proximal stent can be a braided metal mesh. In an example, a proximal stent can be made from shape-memory material. In an example, a proximal stent can be made from a polymer. In an example, a proximal stent can be made with both metal and polymer components. In an example, a proximal stent can have a single layer in its spherical, ellipsoidal, and/or globular configuration and two (or more) layers in its hemispherical, bowl, and/or distally-concave configuration.

In an example, a proximal stent can have a longitudinal axis which spans in a proximal-to-distal direction. Proximal can be defined as being closer to the point of entry into a person's body during delivery through the person's vasculature (in the catheter) to the aneurysm and closer to the aneurysm neck after insertion into the aneurysm sac. In an example, the longitudinal axis of a proximal stent can have a first length while the proximal stent is delivered through the person's vasculature (in the catheter), a second length after expansion into a spherical, ellipsoidal, and/or globular configuration in the aneurysm sac, and a third length after collapse into a hemispherical, bowl, and/or distally-concave configuration in the aneurysm sac. In an example, the second length can be shorter than the first length. In an example, the third length can be shorter than the second length.

In an example, the width of a proximal stent in its hemispherical, bowl, and/or distally-concave configuration can be larger than the width of the aneurysm neck. In an example, the circumference of a proximal stent in its hemispherical, bowl, and/or distally-concave configuration can be larger than the circumference of the aneurysm neck. In an example, the width of a proximal stent in its hemispherical, bowl, and/or distally-concave configuration can be at least 10% larger than the width of the aneurysm neck. In an example, the circumference of a proximal stent in its hemispherical, bowl, and/or distally-concave configuration can be at least 10% larger than the circumference of the aneurysm neck. In an example, the width of a proximal stent in its hemispherical, bowl, and/or distally-concave configuration can be at least 90% of the maximum width of the aneurysm sac (parallel to the aneurysm neck). In an example, the circumference of a proximal stent in its hemispherical, bowl, and/or distally-concave configuration can be at least 90% of the circumference of the maximum circumference of the aneurysm sac (parallel to the aneurysm neck). In an example, a proximal stent can function as a neck bridge, reducing or completely blocking blood flow from the parent vessel into the aneurysm sac.

In an example, a proximal stent can be made by binding each end of a tubular mesh. In an example, a proximal stent can be made by binding and inverting ends of a tubular mesh. In an example, bound and/or inverted ends of a proximal stent can both extend into the interior of the stent in its spherical, ellipsoidal, and/or globular configuration. In an example, a distal bound and/or inverted end of a proximal stent can extend into the interior of the stent in its spherical, ellipsoidal, and/or globular configuration and a proximal bound and/or inverted end of the proximal stent can extend outward from the stent in its spherical, ellipsoidal, and/or globular configuration. In an example, a proximal bound and/or inverted end of a proximal stent can extend into the interior of the stent in its spherical, ellipsoidal, and/or globular configuration and a distal bound and/or inverted end of the proximal stent can extend outward from the stent in its spherical, ellipsoidal, and/or globular configuration.

In an example, there can be an opening and/or lumen through a proximal stent through which embolic members and/or material is inserted into the flexible net or mesh. In an example, this opening and/or lumen can be centrally-located with respect to the proximal surface of the proximal stent. In an example, this opening and/or lumen can be centrally-located with respect to the longitudinal axis of the proximal stent. In an example, this opening and/or lumen can be an opening and/or lumen through a hub into which proximal ends of braided wires or tubes of the stent are bound or attached. In an example, this opening and/or lumen can be off-axial with respect to the longitudinal axis of the proximal stent.

In an example, these can be a closure mechanism which closes an opening and/or lumen after embolic members and/or material has been inserted into a flexible net or mesh. In an example, this closure mechanism can be selected from the group consisting of: valve; electric detachment mechanism; elastic ring or band; threaded mechanism; sliding cover; sliding plug; filament loop; and electromagnetic solenoid. In an example, a closure mechanism can be a leaflet valve. In an example, a closure mechanism can be a one-way valve. In an example, a valve can allow embolic members and/or material to enter a flexible net or mesh through an opening, but not allow the embolic members and/or material to exit the net or mesh through the opening.

In an example, a proximal stent can self-expand into its spherical, ellipsoidal, and/or globular configuration when it is released from the catheter into the aneurysm sac. In this example, the proximal stent can be compressed from its spherical, ellipsoidal, and/or globular configuration to its hemispherical, bowl, and/or distally-concave configuration by pressure from accumulating embolic members and/or material in the flexible net or mesh. In an example, these embolic members and/or material can be delivered into the flexible net or mesh by the person deploying the device.

In another example, a proximal stent can be compressed from its spherical, ellipsoidal, and/or globular configuration to its hemispherical, bowl, and/or distally-concave configuration by a wire, cord, and/or filament which pulls the distal end of the stent in a proximal direction (e.g. down from the dome of the aneurysm sac toward the aneurysm neck). In an example, this wire, cord, and/or filament can be pulled remotely by the person deploying the device. In another example, a proximal stent can be compressed from its spherical, ellipsoidal, and/or globular configuration to its hemispherical, bowl, and/or distally-concave configuration by application of electromagnetic energy to the proximal stent. In an example, this electromagnetic energy can be activated remotely by the person deploying the device.

In an example, a proximal stent can be inside the flexible net or mesh. In an example, the flexible net or mesh can be attached to the proximal stent. In an example, an opening and/or lumen through the proximal stent can be aligned with an opening and/or lumen in the flexible net or mesh, wherein embolic members and/or material are delivered through both openings into the flexible net or mesh. In an example, a flexible net or mesh can be folded and/or compressed when it is inserted into the aneurysm sac, but expand as it is filled with embolic members and/or material. In an example, a flexible net or mesh can have radial folds as it is delivered through a catheter to an aneurysm sac. In an example, a flexible net or mesh can have longitudinal folds as it is delivered through a catheter to an aneurysm sac. In an example, a flexible net or mesh can have cross-sectional folds as it is delivered through a catheter to an aneurysm sac.

In an example, a proximal stent can have a spherical shape after having been inserted into an aneurysm sac and then be collapsed into a hemispherical shape which covers the aneurysm neck. In an example, a proximal stent can have an ellipsoidal shape after having been inserted into an aneurysm sac and then be collapsed into a half-ellipsoidal shape which covers the aneurysm neck. In an example, a proximal stent can have a globular shape after having been inserted into an aneurysm sac and then be collapsed into a paraboloidal shape which covers the aneurysm neck. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere.

In an example, a proximal stent can have a spherical shape after having been inserted into an aneurysm sac and then be collapsed into a hemispherical shape which covers the aneurysm neck, wherein the hemispherical shape has a central opening and/or lumen through which embolic members and/or material is inserted into the aneurysm sac. In an example, a proximal stent can have an ellipsoidal shape after having been inserted into an aneurysm sac and then be collapsed into a half-ellipsoidal shape which covers the aneurysm neck, wherein the hemispherical shape has a central opening and/or lumen through which embolic members and/or material is inserted into the aneurysm sac. In an example, a proximal stent can have a globular shape after having been inserted into an aneurysm sac and then be collapsed into a paraboloidal shape which covers the aneurysm neck, wherein the hemispherical shape has a central opening and/or lumen through which embolic members and/or material is inserted into the aneurysm sac. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere, wherein there are central openings and/or lumens through the proximal and distal surfaces through which embolic members and/or material is inserted into the aneurysm sac.

In an example, a proximal stent can have a spherical shape after having been inserted into an aneurysm sac and then be collapsed into a hemispherical shape which covers the aneurysm neck, wherein the hemispherical shape has an off-axis opening and/or lumen through which embolic members and/or material is inserted into the aneurysm sac. In an example, a proximal stent can have an ellipsoidal shape after having been inserted into an aneurysm sac and then be collapsed into a half-ellipsoidal shape which covers the aneurysm neck, wherein the hemispherical shape has an off-axis opening and/or lumen through which embolic members and/or material is inserted into the aneurysm sac. In an example, a proximal stent can have a globular shape after having been inserted into an aneurysm sac and then be collapsed into a paraboloidal shape which covers the aneurysm neck, wherein the hemispherical shape has an off-axis opening and/or lumen through which embolic members and/or material is inserted into the aneurysm sac. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere, wherein there are off-axis openings and/or lumens through the proximal and distal surfaces through which embolic members and/or material is inserted into the aneurysm sac.

In an example, a distal portion (e.g. the distal half) of a proximal stent can have a lower durometer than the proximal portion (e.g. the proximal half) of the proximal stent. In an example, a distal portion (e.g. the distal half) of a proximal stent can be more flexible than the proximal portion (e.g. the proximal half) of the proximal stent. In an example, a distal portion (e.g. the distal half) of a proximal stent can be less dense than the proximal portion (e.g. the proximal half) of the proximal stent. In an example, a distal portion (e.g. the distal half) of a proximal stent can be more porous dense than the proximal portion (e.g. the proximal half) of the proximal stent.

In an example, a flexible net or mesh can be made from a flexible polymer. In an example, a flexible net or mesh can be made from an elastic and/or stretchable polymer. In an example, a flexible net or mesh can be elastic and/or stretchable and can expand as it is filled with embolic members and/or material. In an example, a flexible net or mesh can be sufficiently flexible to conform to the shape of even an irregularly-shaped aneurysm sac as the net or mesh is filled with embolic members and/or material. In an example, a flexible net or mesh can be sufficiently flexible to conform to the shape of even an irregularly-shaped (e.g. non-spherical) aneurysm sac as the net or mesh is filled with embolic members and/or material.

In an example, a flexible net or mesh can be made from material with a lower durometer than the material used to make the proximal stent. In an example, the net or mesh can be made from material with a greater elasticity than the material used to make the proximal stent. In an example, the net or mesh can be made from material which is more stretchable than the material used to make the proximal stent. In an example, the net or mesh can be made from material which is more conformable than the material used to make the proximal stent. In an example, the net or mesh can be made from material with less strength than the material used to make the proximal stent. In an example, a net or mesh can be more porous than the proximal stent. In an example, a net or mesh can be less dense than the proximal stent. In an example, a net or mesh can be more permeable to liquid than the proximal stent.

In an example, openings or holes in a flexible net or mesh can be smaller than the size (e.g. diameter, width, and/or length) of embolic members and/or material which is inserted into the net or mesh so that the embolic members and/or material do not escape out of the net or mesh. In an example, openings or holes in a flexible net or mesh can less than half of the size (e.g. diameter, width, and/or length) of embolic members and/or material which is inserted into the net or mesh so that the embolic members and/or material do not escape out of the net or mesh. In an example, openings or holes in a flexible net or mesh can have a size which is less than half of the smallest diameter and/or width of embolic members and/or material which is inserted into the net or mesh so that the embolic members and/or material do not escape out of the net or mesh. In an example, openings or holes in a flexible net or mesh can have a size which less than half of the smallest length of embolic members and/or material which is inserted into the net or mesh so that the embolic members and/or material do not escape out of the net or mesh.

In an example, embolic members and/or material inserted into the flexible net or mesh can be microspheres or microballs. In an example, embolic members and/or material inserted into the flexible net or mesh can be microsponges. In an example, embolic members and/or material inserted into the flexible net or mesh can be pieces of foam. In an example, embolic members and/or material inserted into the flexible net or mesh can be microbeads. In an example, embolic members and/or material inserted into the flexible net or mesh can be pieces of hydrogel. In an example, embolic members and/or material inserted into the flexible net or mesh can be metal embolic coils. In an example, embolic members and/or material inserted into the flexible net or mesh can be embolic ribbons. In an example, embolic members and/or material inserted into the flexible net or mesh can be yarns or filaments. In an example, embolic members and/or material can be polymer strands or coils. In an example, accumulation of embolic members and/or material in an aneurysm sac can compress a proximal stent from a spherical, ellipsoidal, and/or globular configuration to a hemispherical, bowl-shaped, and/or distally-concave configuration by pressing against the distal surface of the proximal stent.

In an example, embolic members and/or material inserted into the flexible net or mesh can be microspheres or microballs connected by a longitudinal wire, cord, and/or filament (e.g. in a "string-of-pearls" configuration). In an example, embolic members and/or material inserted into the flexible net or mesh can be microsponges connected by a longitudinal wire, cord, and/or filament (e.g. in a "string-of-pearls" configuration). In an example, embolic members and/or material inserted into the flexible net or mesh can be pieces of foam connected by a longitudinal wire, cord, and/or filament (e.g. in a "string-of-pearls" configuration). In an example, embolic members and/or material inserted into the flexible net or mesh can be microbeads connected by a longitudinal wire, cord, and/or filament (e.g. in a "string-of-pearls" configuration).

In an example, embolic members and/or material inserted into the flexible net or mesh can be pieces of hydrogel connected by a longitudinal wire, cord, and/or filament (e.g. in a "string-of-pearls" configuration). In an example, embolic members and/or material inserted into the flexible net or mesh can be embolic coils connected by a longitudinal wire, cord, and/or filament (e.g. in a "string-of-pearls" configuration). In an example, embolic members and/or material inserted into the flexible net or mesh can be embolic ribbons connected by a longitudinal wire, cord, and/or filament (e.g. in a "string-of-pearls" configuration). In an example, embolic members and/or material inserted into the flexible net or mesh can be yarns or filaments connected by a longitudinal wire, cord, and/or filament (e.g. in a "string-of-pearls" configuration).

In an example, embolic members and/or material inserted into the flexible net or mesh can be liquid which congeals and/or solidifies. In an example, embolic members and/or material inserted into the flexible net or mesh can be a polymer which congeals and/or solidifies. In an example, embolic members and/or material inserted into the flexible net or mesh can be a liquid embolic material. In an example, embolic members and/or material inserted into the flexible net or mesh can be hydrogel material. In an example, embolic members and/or material inserted into the flexible net or mesh can be congealing adhesive material. In an example, accumulation of embolic members and/or material in an aneurysm sac can compress a proximal stent from a spherical, ellipsoidal, and/or globular configuration to a hemispherical, bowl-shaped, and/or distally-concave configuration by pressing against the distal surface of the proximal stent. Other example variations discussed elsewhere in this disclosure or in priority-linked disclosures can also be applied to this example where relevant.

FIGS. 13 through 16 show four sequential views of an intrasacular aneurysm occlusion device comprising: a proximal stent 1301, wherein the proximal stent is inserted into an aneurysm sac, expanded within the aneurysm sac into a spherical, ellipsoidal, and/or globular configuration, and then collapsed within the aneurysm sac into a hemispherical, bowl, and/or distally-concave configuration which covers the aneurysm neck; embolic members and/or material 1501, wherein the embolic members and/or material is inserted into a distal portion of the aneurysm sac, thereby exerting pressure on the distal surface of the proximal stent and compressing the proximal stent from its spherical, ellipsoidal, and/or globular configuration to its hemispherical, bowl, and/or distally-concave configuration; and a catheter and/or other lumen 1302, wherein the embolic members and/or material is delivered through the catheter and/or other lumen into the distal portion of the aneurysm sac.

Figure 13:
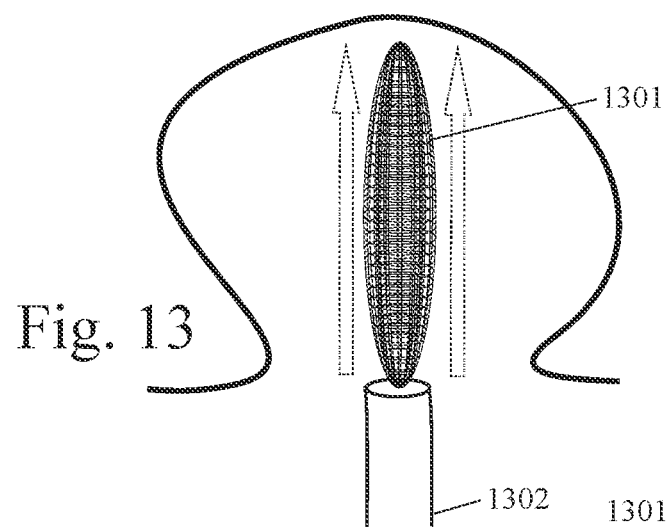
FIGS. 13 through 16 show four sequential views of an intrasacular aneurysm occlusion device with a proximal stent which is compressed from a globular to a bowl-shaped configuration and embolic members/material inserted into a distal portion of the aneurysm sac, wherein the proximal stent is compressed by pressure from accumulating embolic members/material.
Figure 14:
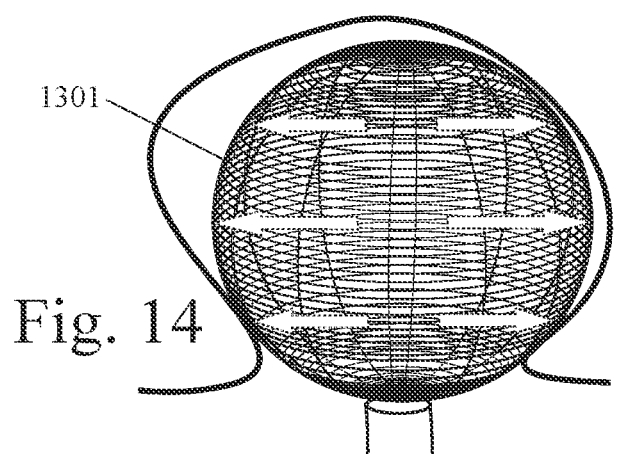
Figure 15:
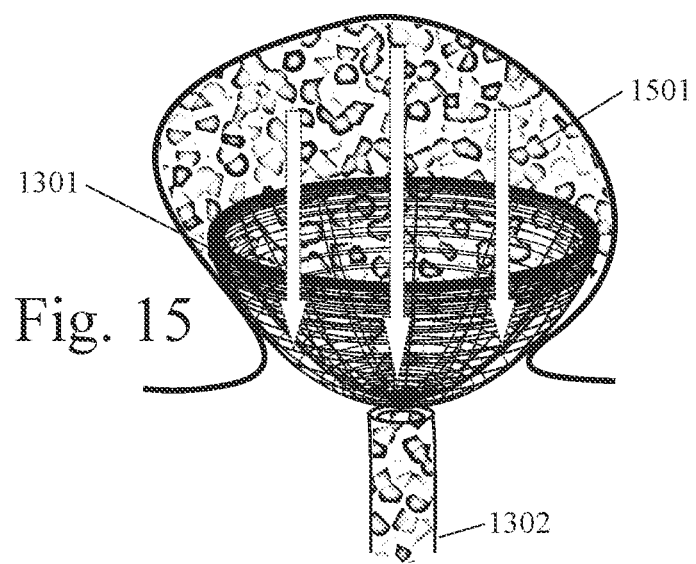
Figure 16:
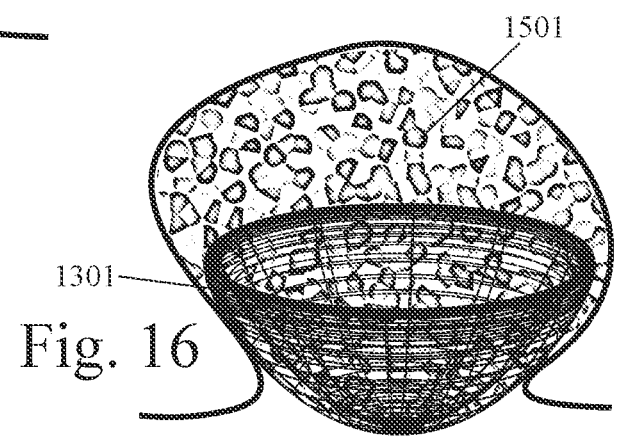

FIG. 13 shows this device at a first point in time when the device is exiting a catheter into an aneurysm sac. FIG. 14 shows this device at a second point in time when the cross-sectional width of the proximal stent is expanding and the stent is transitioning into its spherical, ellipsoidal, and/or globular configuration. FIG. 15 shows this device at a third point in time as the distal portion of the aneurysm sac is being filled with embolic members and/or material, exerting pressure on the proximal stent which is collapsing into its hemispherical, bowl-shaped, and/or distally-concave configuration. FIG. 16 shows this device at a fourth point in time after: the distal portion of the aneurysm sac has been completely filled with embolic members and/or material; the proximal stent has been compressed into its hemispherical, bowl-shaped, and/or distally-concave configuration; and the catheter has been removed.

In an example, a proximal stent can be made from metal. In an example, a proximal stent can be made from Nitinol. In an example, a proximal stent can be a flexible metal mesh. In an example, a proximal stent can be a braided metal mesh. In an example, a proximal stent can be made from shape-memory material. In an example, a proximal stent can be made from a polymer. In an example, a proximal stent can be made with both metal and polymer components. In an example, a proximal stent can have a single layer in its spherical, ellipsoidal, and/or globular configuration and two (or more) layers in its hemispherical, bowl, and/or distally-concave configuration.

In an example, a proximal stent can have a longitudinal axis which spans in a proximal-to-distal direction. Proximal can be defined as being closer to the point of entry into a person's body during delivery through the person's vasculature (in the catheter) to the aneurysm and closer to the aneurysm neck after insertion into the aneurysm sac. In an example, the longitudinal axis of a proximal stent can have a first length while the proximal stent is delivered through the person's vasculature (in the catheter), a second length after expansion into a spherical, ellipsoidal, and/or globular configuration in the aneurysm sac, and a third length after collapse into a hemispherical, bowl, and/or distally-concave configuration in the aneurysm sac. In an example, the second length can be shorter than the first length. In an example, the third length can be shorter than the second length.

In an example, the width of a proximal stent in its hemispherical, bowl, and/or distally-concave configuration can be larger than the width of the aneurysm neck. In an example, the circumference of a proximal stent in its hemispherical, bowl, and/or distally-concave configuration can be larger than the circumference of the aneurysm neck. In an example, the width of a proximal stent in its hemispherical, bowl, and/or distally-concave configuration can be at least 10% larger than the width of the aneurysm neck. In an example, the circumference of a proximal stent in its hemispherical, bowl, and/or distally-concave configuration can be at least 10% larger than the circumference of the aneurysm neck. In an example, the width of a proximal stent in its hemispherical, bowl, and/or distally-concave configuration can be at least 90% of the maximum width of the aneurysm sac (parallel to the aneurysm neck). In an example, the circumference of a proximal stent in its hemispherical, bowl, and/or distally-concave configuration can be at least 90% of the circumference of the maximum circumference of the aneurysm sac (parallel to the aneurysm neck). In an example, a proximal stent can function as a neck bridge, reducing or completely blocking blood flow from the parent vessel into the aneurysm sac.

In an example, a proximal stent can be made by binding each end of a tubular mesh. In an example, a proximal stent can be made by binding and inverting ends of a tubular mesh. In an example, bound and/or inverted ends of a proximal stent can both extend into the interior of the stent in its spherical, ellipsoidal, and/or globular configuration. In an example, a distal bound and/or inverted end of a proximal stent can extend into the interior of the stent in its spherical, ellipsoidal, and/or globular configuration and a proximal bound and/or inverted end of the proximal stent can extend outward from the stent in its spherical, ellipsoidal, and/or globular configuration. In an example, a proximal bound and/or inverted end of a proximal stent can extend into the interior of the stent in its spherical, ellipsoidal, and/or globular configuration and a distal bound and/or inverted end of the proximal stent can extend outward from the stent in its spherical, ellipsoidal, and/or globular configuration.

In an example, there can be an opening and/or lumen through a proximal stent through which embolic members and/or material is inserted into a distal portion of the aneurysm sac. In an example, this opening and/or lumen can be centrally-located with respect to the proximal surface of the proximal stent. In an example, this opening and/or lumen can be centrally-located with respect to the longitudinal axis of the proximal stent. In an example, this opening and/or lumen can be an opening and/or lumen through a hub into which proximal ends of braided wires or tubes of the stent are bound or attached. In an example, this opening and/or lumen can be off-axial with respect to the longitudinal axis of the proximal stent.

In an example, these can be a closure mechanism which closes an opening and/or lumen after embolic members and/or material has been inserted into the distal portion of the aneurysm sac. In an example, this closure mechanism can be selected from the group consisting of: valve; electric detachment mechanism; elastic ring or band; threaded mechanism; sliding cover; sliding plug; filament loop; and electromagnetic solenoid. In an example, a closure mechanism can be a leaflet valve. In an example, a closure mechanism can be a one-way valve. In an example, a valve can allow embolic members and/or material to enter a distal portion of the aneurysm sac, but not allow the embolic members and/or material to exit the aneurysm sac through the opening.

In an example, a proximal stent can self-expand into its spherical, ellipsoidal, and/or globular configuration when it is released from the catheter into the aneurysm sac. In this example, the proximal stent is compressed from its spherical, ellipsoidal, and/or globular configuration to its hemispherical, bowl, and/or distally-concave configuration by pressure from accumulating embolic members and/or material in the distal portion of the aneurysm sac. In an example, these embolic members and/or material can be delivered into a distal portion of the aneurysm sac by the person deploying the device.

In another example, a proximal stent can be compressed from its spherical, ellipsoidal, and/or globular configuration to its hemispherical, bowl, and/or distally-concave configuration by a wire, cord, and/or filament which pulls the distal end of the stent in a proximal direction (e.g. down from the dome of the aneurysm sac toward the aneurysm neck). In an example, this wire, cord, and/or filament can be pulled remotely by the person deploying the device. In another example, a proximal stent can be compressed from its spherical, ellipsoidal, and/or globular configuration to its hemispherical, bowl, and/or distally-concave configuration by application of electromagnetic energy to the proximal stent. In an example, this electromagnetic energy can be activated remotely by the person deploying the device.

In an example, a proximal stent can have a spherical shape after having been inserted into an aneurysm sac and then be collapsed into a hemispherical shape which covers the aneurysm neck. In an example, a proximal stent can have an ellipsoidal shape after having been inserted into an aneurysm sac and then be collapsed into a half-ellipsoidal shape which covers the aneurysm neck. In an example, a proximal stent can have a globular shape after having been inserted into an aneurysm sac and then be collapsed into a paraboloidal shape which covers the aneurysm neck. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere.

In an example, a proximal stent can have a spherical shape after having been inserted into an aneurysm sac and then be collapsed into a hemispherical shape which covers the aneurysm neck, wherein the hemispherical shape has a central opening and/or lumen through which embolic members and/or material is inserted into the aneurysm sac. In an example, a proximal stent can have an ellipsoidal shape after having been inserted into an aneurysm sac and then be collapsed into a half-ellipsoidal shape which covers the aneurysm neck, wherein the hemispherical shape has a central opening and/or lumen through which embolic members and/or material is inserted into the aneurysm sac. In an example, a proximal stent can have a globular shape after having been inserted into an aneurysm sac and then be collapsed into a paraboloidal shape which covers the aneurysm neck, wherein the hemispherical shape has a central opening and/or lumen through which embolic members and/or material is inserted into the aneurysm sac. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere, wherein there are central openings and/or lumens through the proximal and distal surfaces through which embolic members and/or material is inserted into the aneurysm sac.

In an example, a proximal stent can have a spherical shape after having been inserted into an aneurysm sac and then be collapsed into a hemispherical shape which covers the aneurysm neck, wherein the hemispherical shape has an off-axis opening and/or lumen through which embolic members and/or material is inserted into the aneurysm sac. In an example, a proximal stent can have an ellipsoidal shape after having been inserted into an aneurysm sac and then be collapsed into a half-ellipsoidal shape which covers the aneurysm neck, wherein the hemispherical shape has an off-axis opening and/or lumen through which embolic members and/or material is inserted into the aneurysm sac. In an example, a proximal stent can have a globular shape after having been inserted into an aneurysm sac and then be collapsed into a paraboloidal shape which covers the aneurysm neck, wherein the hemispherical shape has an off-axis opening and/or lumen through which embolic members and/or material is inserted into the aneurysm sac. In an example, a proximal stent can have a spherical, ellipsoidal, and/or globular shape after having been inserted into an aneurysm sac and then be collapsed into a shape whose proximal surface is hemispherical and/or bowl-shaped and whose distal surface is a revolution of a parabola or hemisphere, wherein there are off-axis openings and/or lumens through the proximal and distal surfaces through which embolic members and/or material is inserted into the aneurysm sac.

In an example, a distal portion (e.g. the distal half) of a proximal stent can have a lower durometer than the proximal portion (e.g. the proximal half) of the proximal stent. In an example, a distal portion (e.g. the distal half) of a proximal stent can be more flexible than the proximal portion (e.g. the proximal half) of the proximal stent. In an example, a distal portion (e.g. the distal half) of a proximal stent can be less dense than the proximal portion (e.g. the proximal half) of the proximal stent. In an example, a distal portion (e.g. the distal half) of a proximal stent can be more porous dense than the proximal portion (e.g. the proximal half) of the proximal stent.

In an example, embolic members and/or material inserted into a distal portion of the aneurysm sac can be microspheres or microballs. In an example, embolic members and/or material inserted into a distal portion of the aneurysm sac can be microsponges. In an example, embolic members and/or material inserted into a distal portion of the aneurysm sac can be pieces of foam. In an example, embolic members and/or material inserted into a distal portion of the aneurysm sac can be microbeads. In an example, embolic members and/or material inserted into a distal portion of the aneurysm sac can be pieces of hydrogel. In an example, embolic members and/or material inserted into a distal portion of the aneurysm sac can be metal embolic coils. In an example, embolic members and/or material inserted into a distal portion of the aneurysm sac can be embolic ribbons. In an example, embolic members and/or material inserted into a distal portion of the aneurysm sac can be yarns or filaments. In an example, embolic members and/or material can be polymer strands or coils. In an example, accumulation of embolic members and/or material in an aneurysm sac can compress a proximal stent from a spherical, ellipsoidal, and/or globular configuration to a hemispherical, bowl-shaped, and/or distally-concave configuration by pressing against the distal surface of the proximal stent.

In an example, embolic members and/or material inserted into a distal portion of the aneurysm sac can be microspheres or microballs connected by a longitudinal wire, cord, and/or filament (e.g. in a "string-of-pearls" configuration). In an example, embolic members and/or material inserted into a distal portion of the aneurysm sac can be microsponges connected by a longitudinal wire, cord, and/or filament (e.g. in a "string-of-pearls" configuration). In an example, embolic members and/or material inserted into a distal portion of the aneurysm sac can be pieces of foam connected by a longitudinal wire, cord, and/or filament (e.g. in a "string-of-pearls" configuration). In an example, embolic members and/or material inserted into a distal portion of the aneurysm sac can be microbeads connected by a longitudinal wire, cord, and/or filament (e.g. in a "string-of-pearls" configuration).

In an example, embolic members and/or material inserted into a distal portion of the aneurysm sac can be pieces of hydrogel connected by a longitudinal wire, cord, and/or filament (e.g. in a "string-of-pearls" configuration). In an example, embolic members and/or material inserted into a distal portion of the aneurysm sac can be embolic coils connected by a longitudinal wire, cord, and/or filament (e.g. in a "string-of-pearls" configuration). In an example, embolic members and/or material inserted into a distal portion of the aneurysm sac can be embolic ribbons connected by a longitudinal wire, cord, and/or filament (e.g. in a "string-of-pearls" configuration). In an example, embolic members and/or material inserted into a distal portion of the aneurysm sac can be yarns or filaments connected by a longitudinal wire, cord, and/or filament (e.g. in a "string-of-pearls" configuration).

In an example, embolic members and/or material inserted into a distal portion of the aneurysm sac can be liquid which congeals and/or solidifies. In an example, embolic members and/or material inserted into a distal portion of the aneurysm sac can be a polymer which congeals and/or solidifies. In an example, embolic members and/or material inserted into a distal portion of the aneurysm sac can be a liquid embolic material. In an example, embolic members and/or material inserted into a distal portion of the aneurysm sac can be hydrogel material. In an example, embolic members and/or material inserted into a distal portion of the aneurysm sac can be congealing adhesive material. In an example, accumulation of embolic members and/or material in an aneurysm sac can compress a proximal stent from a spherical, ellipsoidal, and/or globular configuration to a hemispherical, bowl-shaped, and/or distally-concave configuration by pressing against the distal surface of the proximal stent. Other example variations discussed elsewhere in this disclosure or in priority-linked disclosures can also be applied to this example where relevant.

I claim:

1. An intrasacular aneurysm occlusion device comprising:
    a proximal stent, wherein the proximal stent is inserted into an aneurysm sac, expanded within the aneurysm sac into a spherical, ellipsoidal, and/or globular configuration, and then collapsed within the aneurysm sac into a hemispherical, bowl, and/or distally-concave configuration which covers the aneurysm neck;
    embolic members and/or material, wherein the embolic members and/or material is inserted into a distal portion of the aneurysm sac, thereby exerting pressure on the distal surface of the proximal stent and compressing the proximal stent from its spherical, ellipsoidal, and/or globular configuration to its hemispherical, bowl, and/or distally-concave configuration; and
    a catheter and/or other lumen, wherein the embolic members and/or material is delivered through the catheter and/or other lumen into the distal portion of the aneurysm sac.

2. An intrasacular aneurysm occlusion device comprising:
    a proximal stent, wherein the proximal stent is inserted into an aneurysm sac, expanded within the aneurysm sac into a spherical, ellipsoidal, and/or globular configuration, and then collapsed within the aneurysm sac into a hemispherical, bowl, and/or distally-concave configuration which covers the aneurysm neck;
embolic members and/or material, wherein the embolic members and/or material is inserted into a distal portion of the aneurysm sac;
a catheter and/or other lumen, wherein the embolic members and/or material is delivered through the catheter and/or other lumen into the distal portion of the aneurysm sac; and
a wire, cord, and/or filament, wherein the wire, cord, and/or filament is pulled to collapse the proximal stent into the hemispherical, bowl, and/or distally concave shape.

3. An intrasacular aneurysm occlusion device comprising:
a proximal stent, wherein the proximal stent is inserted into an aneurysm sac, expanded within the aneurysm sac into a spherical, ellipsoidal, and/or globular configuration, and then collapsed within the aneurysm sac into a hemispherical, bowl, and/or distally-concave configuration which covers the aneurysm neck;
a distal flexible mesh or net, wherein the flexible mesh or net is inserted into the aneurysm sac, and wherein the most distal portion of the flexible mesh or net is farther from the aneurysm neck than the most distal portion of the stent in its hemispherical, bowl, and/or distally-concave configuration;
embolic members and/or material, wherein the embolic members and/or material is inserted into the flexible mesh or net, wherein insertion of the embolic members and/or material into the flexible mesh or net expands the flexible mesh or net to conform to the walls of even an irregularly-shaped aneurysm sac, and wherein insertion of the embolic members and/or material into the flexible mesh or net also helps to keep the stent in place covering the aneurysm neck;
a catheter and/or other lumen, wherein the embolic members and/or material is delivered through the catheter and/or other lumen into the flexible mesh or net; and
a wire, cord, and/or filament, wherein the wire, cord, and/or filament is pulled to collapse the proximal stent into the hemispherical, bowl, and/or distally concave shape.

* * * * *